(12) United States Patent
Elia et al.

(10) Patent No.: US 10,835,178 B2
(45) Date of Patent: Nov. 17, 2020

(54) SYSTEMS AND METHODS FOR SENSING LUNG FLUID AND FUNCTIONALITY

(71) Applicant: ART Medical Ltd., Netanya (IL)

(72) Inventors: Liron Elia, Kiryat-Ata (IL); Gavriel J. Iddan, Haifa (IL)

(73) Assignee: ART Medical Ltd., Netanya (IL)

(*) Notice: Subject to any disclaimer, the term of this patent is extended or adjusted under 35 U.S.C. 154(b) by 0 days.

(21) Appl. No.: 16/467,078

(22) PCT Filed: Dec. 6, 2017

(86) PCT No.: PCT/IB2017/057702
§ 371 (c)(1),
(2) Date: Jun. 6, 2019

(87) PCT Pub. No.: WO2018/104888
PCT Pub. Date: Jun. 14, 2018

(65) Prior Publication Data
US 2019/0313970 A1    Oct. 17, 2019

Related U.S. Application Data

(60) Provisional application No. 62/430,378, filed on Dec. 6, 2016.

(51) Int. Cl.
*A61B 5/00* (2006.01)
*A61J 15/00* (2006.01)
(Continued)

(52) U.S. Cl.
CPC .......... *A61B 5/4878* (2013.01); *A61B 5/0535* (2013.01); *A61B 5/0537* (2013.01);
(Continued)

(58) Field of Classification Search
CPC ... A61B 5/4878; A61B 5/4875; A61B 5/0537; A61B 5/0538; A61B 5/6853;
(Continued)

(56) References Cited

U.S. PATENT DOCUMENTS

2005/0124908 A1* 6/2005 Belalcazar ........... A61B 5/0537
600/547
2005/0137480 A1* 6/2005 Alt ....................... A61B 5/0031
600/508

(Continued)

FOREIGN PATENT DOCUMENTS

WO    WO 2018/104888    6/2018

OTHER PUBLICATIONS

International Preliminary Report on Patentability Dated Mar. 19, 2019 From the International Preliminary Examining Authority Re. Application No. PCT/IB2017/057702. (27 Pages).

(Continued)

*Primary Examiner* — Matthew Kremer
*Assistant Examiner* — Avery M Foley

(57) ABSTRACT

An apparatus for monitoring for accumulation of lung fluid comprises a feeding tube having first electrode(s) positioned thereon for electrical contact with tissue of an esophagus of a target patient including a lower esophageal sphincter (LES) and/or tissue in proximity to the LES, second electrode(s) sized and shaped for contacting skin of the target patient, and a non-transitory memory having stored thereon code instructions for applying alternating current(s) to pair(s) of first and second electrodes, measuring a voltage over the pair(s), and computing an estimate of a change of lung fluid relative to a baseline in lung(s) of the target patient according to the applied alternating current and measured voltage, wherein the applying, the measuring, and the computing the estimate of the change in lung fluid are iteratively executed for monitoring the target patient for accumulation of lung fluid while the feeding tube is in use.

26 Claims, 12 Drawing Sheets

(51) Int. Cl.
*A61B 5/053* (2006.01)
*A61B 5/02* (2006.01)

(52) U.S. Cl.
CPC .......... *A61B 5/0538* (2013.01); *A61B 5/6853* (2013.01); *A61J 15/0003* (2013.01); *A61J 15/0049* (2013.01); *A61J 15/0084* (2015.05); *A61B 5/02042* (2013.01)

(58) Field of Classification Search
CPC ..... A61B 5/687; A61B 5/6871; A61B 5/0535; A61B 5/02042; A61J 15/0084; A61J 15/0088; A61J 15/008; A61J 15/0003; A61J 15/00; A61J 15/0026; A61J 15/003; A61J 15/0038; A61J 15/0042; A61J 15/0049
See application file for complete search history.

(56) References Cited

U.S. PATENT DOCUMENTS

| | | | | |
|---|---|---|---|---|
| 2008/0154191 A1* | 6/2008 | Gobel | ................... | A61B 5/037 604/101.05 |
| 2010/0030133 A1* | 2/2010 | Elia | ....................... | A61B 5/037 604/28 |
| 2010/0174170 A1* | 7/2010 | Razavi | .................. | A61B 5/042 600/371 |
| 2011/0022127 A1* | 1/2011 | Averina | ............... | A61B 5/0537 607/62 |
| 2011/0184274 A1* | 7/2011 | Rosenberg | ........... | A61B 5/0536 600/424 |
| 2012/0165884 A1* | 6/2012 | Xi | ....................... | A61B 5/0537 607/4 |
| 2014/0018696 A1* | 1/2014 | DeArmond | .......... | A61B 5/0538 600/547 |
| 2014/0288384 A1* | 9/2014 | Mulrooney | ........ | A61B 5/04884 600/301 |
| 2015/0025333 A1* | 1/2015 | Weinstein | .......... | A61B 5/02158 600/301 |
| 2015/0297099 A1* | 10/2015 | Arad (Abboud) | ..... | A61B 5/686 600/375 |
| 2015/0374256 A1* | 12/2015 | Skrabal | ................. | A61B 5/721 600/301 |

OTHER PUBLICATIONS

International Search Report and the Written Opinion Dated May 11, 2018 From the International Searching Authority Re. Application No. PCT/IB2017/057702. (21 Pages).
Invitation to Pay Additional Fees, Communication Relating to the Results of the Partial International Search and the Provisional Opinion Dated Feb. 28, 2018 From the International Searching Authority Re. Application No. PCT/IB2017/057702. (16 Pages).
Written Opinion Dated Nov. 23, 2018 From the International Preliminary Examining Authority Re. Application No. PCT/IB2017/057702. (10 Pages).

* cited by examiner

SYSTEMS AND METHODS FOR SENSING LUNG FLUID AND FUNCTIONALITY

RELATED APPLICATIONS

This application is a National Phase of PCT Patent Application No. PCT/IB2017/057702 having International filing date of Dec. 6, 2017, which claims the benefit of priority under 35 USC § 119(e) of U.S. Provisional Patent Application No. 62/430,378 filed on Dec. 6, 2016. The contents of the above applications are all incorporated by reference as if fully set forth herein in their entirety.

BACKGROUND

The present invention, in some embodiments thereof, relates to intra-body fluid measurements and, more specifically, but not exclusively, to systems and methods for sensing lung fluid of a patient.

Pleural effusion is the collection of fluid outside the lungs, in the pleural space of the lungs. Pulmonary edema is the collection of fluid inside lungs, within the alveoli and/or parenchyma. Pleural effusion and/or pulmonary edema may present within patients, for example patients admitted to the intensive care unit (ICU), for example, as a saturation drop.

Pleural effusion and pulmonary edema share some aspects of pathophysiology, for example, resulting from cardiac failure, fluid overload, liver failure, and/or renal failure. For example, failure of the left ventricle of the heart to adequately remove blood from the pulmonary circulation, and/or an injury to the lung parenchyma or vasculature of the lung.

Pulmonary edema leads to airway obstruction and respiratory failure. There are two recognized types of Pulmonary edema:
  Type I follows a sudden, severe episode of upper airway obstruction (such as post-extubation laryngospasm) and may be associated with any cause of acute airway obstruction.
  Type II develops after surgical relief of chronic upper airway obstruction.

The incidence of development of pulmonary edema in acute upper airway obstruction (type I) ranges from 9.6-12% and that in chronic airway obstruction (type II) is 44%. Morbidity and mortality rates range from 11% to 40%.

SUMMARY

According to a first aspect, an apparatus for monitoring a target patient for accumulation of lung fluid, the apparatus comprises: a feeding tube for insertion into a distal end of an esophagus of the target patient, at least one first electrode disposed on the distal end of the feeding tube at a location such that the at least one first electrode is located at the distal end of the esophagus of the target patient when the feeding tube is located within the esophagus and in use and, wherein the at least one first electrode is positioned for electrical contact with the tissue of the esophagus including at least one of a lower esophageal sphincter (LES) and tissue in proximity to the LES, at least one second electrode sized and shaped for contacting the surface of the skin of the target patient, and a non-transitory memory having stored thereon a code for execution by at least one hardware processor of a computing device, the code including instruction for applying at least one alternating current to at least one pair of first and second electrodes, measuring a voltage over the at least one pair of first and second electrodes, and computing an estimate of a change of lung fluid relative to a baseline in at least one lung of the target patient according to the applied alternating current and measured voltage, wherein the applying the at least one alternating current, the measuring the voltage drop, and the computing the estimate of the change in lung fluid are iteratively executed for monitoring the target patient for accumulation of lung fluid while the feeding tube is in use.

According to a second aspect, a method for sensing lung fluid of a target patient, the method comprises: applying at least one alternating current to at least one first electrode, wherein the at least one first electrode is disposed on a distal end of an feeding tube sized and shaped for insertion into a distal end of an esophagus of the target patient, at a location such that the at least one first electrode is located at the distal end of the esophagus of the target patient when the feeding tube is located within the esophagus and in use, wherein the at least one first electrode is positioned for electrical contact with the tissue of the esophagus including at least one of a lower esophageal sphincter (LES) and tissue in proximity to the LES, measuring a voltage drop over at least one pair of a first and second electrode, wherein at least one second electrode is sized and shaped for contacting the surface of the skin of the target patient, and computing an estimate of an change of lung fluid relative to a baseline in at least one lung of the target patient according to the applied alternating current and the measured voltage drop, wherein the applying the at least one alternating current, the measuring the voltage drop, and the computing the estimate of the amount of fluid are iteratively executed for monitoring the target patient while the feeding tube is in use.

The systems, methods, apparatus, and/or code instructions described herein relate to the technical problem of monitoring for accumulation of lung fluid. In particular, continuously (or near continuously, for example, at closely spaced intervals, for example, every minute, 5 minutes, or 10 minutes) monitoring the amount of lung fluid. The technical problem may relate to monitoring for a clinically significant amount of lung fluid, and/or a prediction of a risk of developing a clinically significant amount of lung fluid. The clinically significant amount of lung fluid may affect the patient's breathing, and/or may require treatment (e.g., drainage) and/or further investigation of underlying causes. Prediction of risk of impending accumulation of clinically significant amount of lung fluid may trigger early treatment to prevent the accumulation, for example, treatment of early heart failure before the lung fluid accumulates.

The systems, methods, apparatus, and/or code instructions described herein may relate to the technical problem of safety detecting lung fluid. In contrast, some other approaches are based on an electrode positioned within or in proximity to the heart. When lung fluid is measured by these approaches, current is passed through the heart, which increases the risk of, for example, of an arrhythmia. In contrast, the systems, methods, apparatus, and/or code instructions described herein are based on locating sensor(s) away from the heart, optionally in proximity to the lower esophageal sphincter, which prevent passages of electrical current through the heart, or significantly reduce electrical current through the heart to safe levels. Some other approaches are based on electrodes located externally to the skin of the patient. The current applied between such electrodes may entirely bypass the lung, or mostly bypass the lung, resulting in inaccurate measurements that are unable to correctly sense the amount of lung fluid. In contrast, the systems, methods, apparatus, and/or code instructions described herein are based on sandwiching one or each lung between the electrodes, which directs most or all of the current Some implementations of the systems, methods, apparatus, and/or code instructions described herein improve the performance of existing tubes and/or electrodes, which are positioned with the esophagus of the patient for other reasons, for example, a nasogastric tube for removing fluid from the stomach and/or digestive system of the patient, and/or an enteral feeding tube for delivering enteral feedings to the stomach and/or digestive system of the patient. The impedance readings obtained by the electrodes, which may be obtained for other reasons (e.g., determine a reflux event, monitor correct positioning of the tube, and/or estimate amount of fluid in the stomach) may be further utilized to monitor the patient for accumulation of lung fluid. The patient may be monitored for accumulation of lung fluid while the tube and/or electrodes are utilized for other purposes. For example, while an intubated patient is being enterally fed over a 24 period, the feeding tube is simultaneously utilized for monitoring for accumulation of lung fluid.

The systems, methods, apparatus, and/or code instructions described herein do not simply perform automation of a manual procedure, but perform additional automated features which cannot be performed manually by a human using pencil and/or paper. According to current practice, detection of lung fluid is generally a medical art, based on the physical performing one or more of the following: observation of breathing difficulty, detection of low oxygen saturation, auscultation of the lungs, analysis of a chest x-ray, and performing an analysis of pleural fluid (which is obtained by a painful procedure in which a needle is inserted into the pleural space). Lung fluid is more reliably detected based on images acquired by advanced imaging modalities, for example, computed tomography (CT) and magnetic resonance imaging (MRI), which however are not always available, and take time to analyze. Monitoring the development of lung fluid according to current practice is difficult, and unreliable. Moreover, current methods are based on estimating existing lung fluid, and do not relate to prediction of risk of accumulation of lung fluid. In contrast, the systems, methods, apparatus, and/or code instructions described herein provide real-time, optionally continuous, monitoring of the amount of lung fluid, real-time detection of accumulation of a clinically significant amount of lung fluid, and/or optionally predict a risk of accumulation of an excess amount of lung fluid in the near future. An indication of the monitoring and/or prediction is generated, which provides healthcare workers with early and/or advanced notification for taking preventing action and/or early treatment to avoid complications and/or consequences of delayed diagnosis and treatment.

In a further implementation form of the first and second aspects, the applying, the measuring, and the computing are continuously executed for continuous monitoring of the target patient for accumulation of lung fluid.

In a further implementation form of the first and second aspects, the at least one first electrode is disposed on the distal end of the feeding tube at a location such that the at least one electrode is located at least one of: in proximity to the LES and in contact with the LES of the target patient.

In a further implementation form of the first and second aspects, a plurality of second electrodes are placed on the skin of the target individual at locations corresponding to each of two lungs for independent monitoring of lung fluid of each lung.

In a further implementation form of the first and second aspects, the feeding tube includes an enteral feeding tube having a distal end designed for positioning within the digestive system when in use for enteral feeding.

In a further implementation form of the first and second aspects, the feeding tube includes a nasogastric tube having a distal end designed for positioning within the digestive system when in use.

In a further implementation form of the first and second aspects, the at least one first electrode is associated with a clip-on attachment mechanism that attaches to an off-the-shelf feeding tube.

In a further implementation form of the first and second aspects, the feeding tube includes a catheter having at least one lumen that includes wires for transmission of signals between the at least one first electrode and an externally located at least one hardware processor.

In a further implementation form of the first and second aspects, the at least one first electrode is mounted on an inflatable balloon located at the distal end of the feeding tube, wherein when the inflatable balloon is inflated the at least one first electrode contacts the inner wall of the esophagus.

In a further implementation form of the first and second aspects, the at least one first electrode and the at least one second electrode include electrodes for generating the at least one alternating current and for sensing the generated at least one alternating current.

In a further implementation form of the first and second aspects, the at least one second electrode includes at least one pad electrode designed for contacting the skin of the target patient.

In a further implementation form of the first and second aspects, the computing the estimate of the amount of lung fluid changes in at least one lung of the target patient according to the applied alternating current is indicative of pulmonary edema at a certain lung lobe when the at least one second electrode is positioned on the skin of the target patient corresponding to the certain lung lobe.

In a further implementation form of the first and second aspects, the computing the estimate, based on initial base measurement of the changes of lung fluid in at least one lung of the target patient according to the applied alternating current is indicative of pulmonary effusion of a certain lung when the at least one second electrode is positioned on the skin of the target patient corresponding to the base of the certain lung.

In a further implementation form of the first and second aspects, the system and/or method further comprise code for and/or instructions for differentiating between pulmonary edema and pleural effusion according to an analysis of impedance values measured by at least one second electrode located on skin of the target individual corresponding to the base of at least one lung and impedance values measured by another at least one second electrode located on skin of the target individual corresponding to one or more lobes of the at least one lung.

In a further implementation form of the first and second aspects, the system and/or method further comprise code for and/or instructions for estimating changes in level of fluid within the digestive system based on an analysis of the applied alternating current and measured voltage drop.

In a further implementation form of the first and second aspects, the system and/or method further comprise code for and/or instructions for monitoring a position of the feeding tube within the digestive system based on an analysis of the applied alternating current and measured voltage drop.

In a further implementation form of the first and second aspects, the system and/or method further comprise code for and/or instructions for detecting a gastric reflux event based on an analysis of the applied alternating current and measured voltage drop and distinguishing the reflux event from lung fluid changes.

In a further implementation form of the first and second aspects, the system and/or method further comprise code for and/or instructions for estimating a change in lung function relative to a lung function baseline according to a correlation between change in lung fluid and lung function.

In a further implementation form of the first and second aspects, the system and/or method further comprise code for and/or instructions for comparing lung fluid changes between the left and right lung for differentiation between lung fluid processes that affect both lungs from lung fluid processes that affect one lung more than the other.

In a further implementation form of the first and second aspects, the amount of lung fluid is estimated for the left lung and right lung of the target patient according to measurements performed by a left set of the at least one second electrodes positioned on the left side of the target patient in proximity to the left lung and a right set of the at least one second electrodes positioned on the right side of the target patient in proximity to the right lung and the same set of common at least one first electrodes.

In a further implementation form of the first and second aspects, the estimated of an amount of lung fluid in at least one lung of the target patient is computed based on impedance values computed according to the applied at least one alternating current and sensed voltage.

In a further implementation form of the first and second aspects, the system and/or method further comprise code for and/or instructions for mapping the impedance values to an indication of clinically significant amount of lung fluid.

In a further implementation form of the first and second aspects, the amount of lung fluid is estimated according to a reference set of base values measured from a plurality of sampled individuals that map between measured impedance values and amounts of lung fluids.

In a further implementation form of the first and second aspects, the amount of lung fluid is estimated by code for: computing at least one impedance value corresponding the at least one frequency of the at least one applied current, converting the computed at least one impedance value to an impedance score associated with a time stamp indicative of the time of application of the at least one applied current, and presenting the impedance score as a value on a graph within a graphical user interface (GUI) displayed on a display of a client terminal, wherein an x-axis of the graph denotes the time of application of the at least one applied current and a y-axis of the graph denotes the impedance score.

In a further implementation form of the first and second aspects, the graph includes an indication of a threshold differentiating between clinically significant amount of fluid and clinically insignificant amount of fluid.

In a further implementation form of the first and second aspects, the system and/or method further comprise code for and/or instructions for computing the impedance score according to a member selected from the group consisting of: a real component of a complex impedance value, an imaginary component of a complex impedance value, and a length of a vector computed according to the real and complex components.

In a further implementation form of the first and second aspects, the graph presented within the GUI includes a plurality of impedance scores computed over an interval of time, and further comprising code for: computing a trend line for at least a sub-set of recent impedance scores, and predicting an impending accumulation of a clinically significant change in the amount of lung fluid according to an extension of the trend line that crosses at a future time a threshold differentiating between clinically significant amount of fluid and clinically insignificant amount of fluid.

In a further implementation form of the first and second aspects, the system and/or method further comprise code for and/or instructions for predicting a probability of impending accumulation of clinically significant amount of lung fluid according to at least one of: a correlation value indicative of fit of the trend line to the sub-set of recent impedance scores, and the amount of time in the future when the trend line is predicted to reach the threshold.

In a further implementation form of the first and second aspects, the system and/or method further comprise code for and/or instructions for dynamically computing the trend line by a least square best fit of a line to recent impedance scores within a sliding window, as new impedance scores are plotted on the graph.

In a further implementation form of the first and second aspects, the system and/or method further comprise code for and/or instructions for computing a baseline impedance value indicative of a first amount of fluid in the at least one lung denoted as clinically insignificant, and monitoring measured impedance values to detect a drop in the impedance value below a threshold indicative of a second amount of fluid in the at least one lung denoted as clinically significant.

In a further implementation form of the first and second aspects, the system and/or method further comprise code for and/or instructions for generating an alert when a set of rules is met indicative of an impending accumulation of clinically significant amount of lung fluid according to a defined risk threshold, and transmitting the alert for presentation on at least one of: a client terminal, a mobile device, and a server.

In a further implementation form of the first and second aspects, a probability of the impending accumulating of clinically significant amount of lung fluid is computed according to a direction of a trend line towards threshold denoting accumulation of clinically significant amount of fluid, the trend line computed based on a plurality of impedance values measured over a recent time interval.

In a further implementation form of the first and second aspects, the lung fluid includes at least one of: pleural effusion and lung edema.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
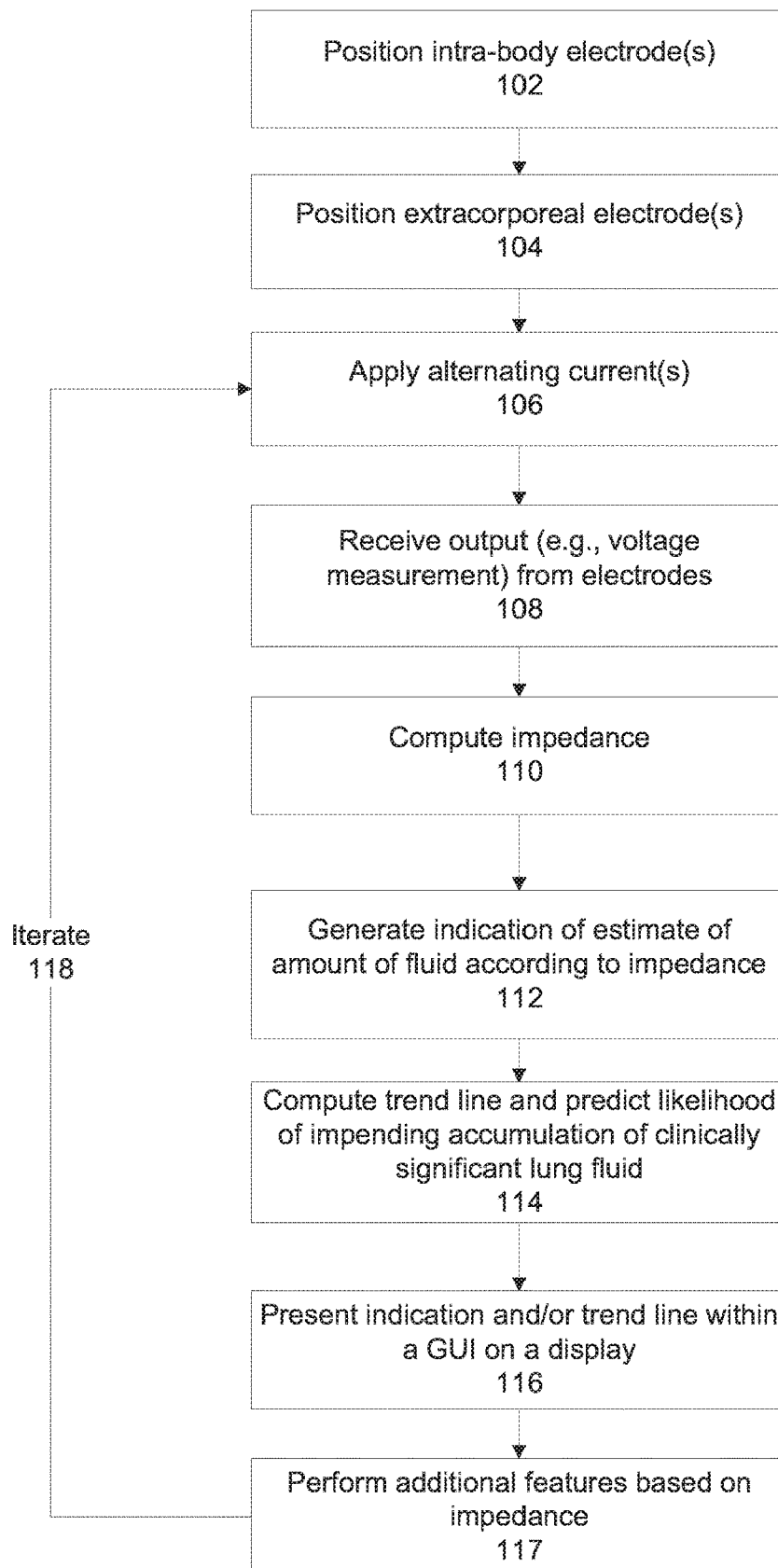
FIG. 1 is a flowchart of a method for sensing lung fluid of a target patient based on at least one electrode positioned within the esophagus and/or stomach of a target patient, in accordance with some embodiments of the present invention.

The present invention, in some embodiments thereof, relates to intra-body fluid measurements and, more specifically, but not exclusively, to systems and methods for sensing lung fluid of a patient.

As used herein, the term lung fluid refers to pleural effusion and/or pulmonary edema. The term lung fluid may refer to one or more types of lung fluid, for example, exudate and/or transudate of various types and blood.

As used herein, the feeding tube may sometimes be interchanged with the term nasogastric tube. For example, rather than a feeding tube (i.e., for delivery of enteral feedings to the stomach and/or digestive system) a nasogastric tube (i.e., for removal of fluid from the stomach and/or digestive system) may be used. It is noted that in some cases a dedicated catheter may be used for monitoring for lung fluid.

An aspect of some embodiments of the present invention relates to systems, methods, an apparatus, and/or code instructions (stored in a data storage device, executable by one or more hardware processor(s)) for sensing lung fluid of a target patient. A feeding tube including at least one intra-body electrode (which may also act as a sensor) at its distal end is located within the esophagus and/or stomach. The intra-body electrode(s) is positioned in proximity to and/or in contact with the lower esophagus sphincter (LES) of the target patient, above and/or below the LES, within the esophagus and/or stomach. One or more alternating currents (AC) at different frequencies are applied between the intra-body electrode(s) and one or more extracorporeal electrode(s) applied to the surface of the skin of the target individual. The alternating current(s) is transmitted between the intra-body electrode(s) and the extracorporeal electrode(s) through the lung(s). An estimated of the amount of lung fluid and/or the change of lung fluid relative to a baseline measurement in one lung or each one of the patient's lungs is computed according to a measurement(s) outputted by the intra-body electrode(s) and/or the extracorporeal electrode(s). Optionally, the estimated of the amount of lung fluid is computed according to an impedance value(s) computed based on the applied AC current and measured voltage.

As used herein, the phrase the estimated amount of lung fluid may sometime be interchanged with the phrase the estimated change of lung fluid relative to a baseline. The systems, methods, apparatus, and/or code instructions described herein may estimate the absolute amount of lung fluid, and/or estimate the change of lung fluid relative to an initial baseline measurement.

The systems, methods, apparatus, and/or code instructions described herein relate to the technical problem of monitoring for accumulation of lung fluid. In particular, continuously (or near continuously, for example, at closely spaced intervals, for example, every minute, 5 minutes, or 10 minutes) monitoring the amount of lung fluid. The technical problem may relate to monitoring for a clinically significant amount of lung fluid, and/or a prediction of a risk of developing a clinically significant amount of lung fluid. The clinically significant amount of lung fluid may affect the patient's breathing, and/or may require treatment (e.g., drainage) and/or further investigation of underlying causes. Prediction of risk of impending accumulation of clinically significant amount of lung fluid may trigger early treatment to prevent the accumulation, for example, treatment of early heart failure before the lung fluid accumulates.

The systems, methods, apparatus, and/or code instructions described herein may relate to the technical problem of safety detecting lung fluid. In contrast, some other approaches are based on an electrode positioned within or in proximity to the heart. When lung fluid is measured by these approaches, current is passed through the heart, which increases the risk of, for example, of an arrhythmia. In contrast, the systems, methods, apparatus, and/or code instructions described herein are based on locating sensor(s) away from the heart, optionally in proximity to the lower esophageal sphincter, which prevent passages of electrical current through the heart, or significantly reduce electrical current through the heart to safe levels. Some other approaches are based on electrodes located externally to the skin of the patient. The current applied between such electrodes may entirely bypass the lung, or mostly bypass the lung, resulting in inaccurate measurements that are unable to correctly sense the amount of lung fluid. In contrast, the systems, methods, apparatus, and/or code instructions described herein are based on sandwiching one or each lung between the electrodes, which directs most or all of the current.

Some implementations of the systems, methods, apparatus, and/or code instructions described herein improve the performance of existing tubes and/or electrodes, which are positioned with the esophagus of the patient for other reasons, for example, a nasogastric tube for removing fluid from the stomach and/or digestive system of the patient, and/or an enteral feeding tube for delivering enteral feedings to the stomach and/or digestive system of the patient. The impedance readings obtained by the electrodes, which may be obtained for other reasons (e.g., determine a reflux event, monitor correct positioning of the tube, and/or estimate amount of fluid in the stomach) may be further utilized to monitor the patient for accumulation of lung fluid. The patient may be monitored for accumulation of lung fluid while the tube and/or electrodes are utilized for other purposes. For example, while an intubated patient is being enterally fed over a 24 period, the feeding tube is simultaneously utilized for monitoring for accumulation of lung fluid.

The systems, methods, apparatus, and/or code instructions described herein do not simply perform automation of a manual procedure, but perform additional automated features which cannot be performed manually by a human using pencil and/or paper. According to current practice, detection of lung fluid is generally a medical art, based on the physical performing one or more of the following: observation of breathing difficulty, detection of low oxygen saturation, auscultation of the lungs, analysis of a chest x-ray, and performing an analysis of pleural fluid (which is obtained by a painful procedure in which a needle is inserted into the pleural space). Lung fluid is more reliably detected based on images acquired by advanced imaging modalities, for example, computed tomography (CT) and magnetic resonance imaging (MRI), which however are not always available, and take time to analyze. Monitoring the development of lung fluid according to current practice is difficult, and unreliable. Moreover, current methods are based on estimating existing lung fluid, and do not relate to prediction of risk of accumulation of lung fluid. In contrast, the systems, methods, apparatus, and/or code instructions described herein provide real-time, optionally continuous, monitoring of the amount of lung fluid, real-time detection of accumulation of a clinically significant amount of lung fluid, and/or optionally predict a risk of accumulation of an excess amount of lung fluid in the near future. An indication of the monitoring and/or prediction is generated, which provides healthcare workers with early and/or advanced notification for taking preventing action and/or early treatment to avoid complications and/or consequences of delayed diagnosis and treatment.

When the features related to by the systems, methods, apparatus, and/or code instructions described herein are taken as a whole, the combination of the features amounts to significantly more than a simple mathematical calculation of computing impedance value(s) and estimating the amount of lung fluid according to the impedance value(s). The systems, methods, apparatus, and/or code instructions described herein do not merely relate to mathematical computations (e.g., equations), but relate to the particular data collected, stored, and the way the data is collected by electrodes, and optionally performing a prediction of likelihood of an impending accumulation of a clinically significant amount of lung fluid.

The systems, methods, apparatus, and/or code instructions described herein improve an underlying technical process within the technical field of automated patient monitoring, in particular, within the field of automated monitoring of lung fluid.

The systems, methods, apparatus, and/or code instructions described herein provide a unique, particular, and advanced technique of monitoring lung fluid, and optionally predicting likelihood of an impending accumulation of a clinically significant amount of lung fluid.

The systems, methods, apparatus, and/or code instructions described herein are tied to physical real-life components, for example, one or more of: electrode(s) that measure impedance, a feeding tube (e.g., nasogastric tube, enteral feeding tube) on which one or more electrodes are disposed, computational hardware (e.g., hardware processor(s), physical memory device) that analyzes the electrode output, and a display that presents the estimated amount of lung fluid and/or presents the indication of prediction of likelihood of an impending accumulation of a clinically significant amount of lung fluid.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the term clinically significant lung fluid, or lung fluid, refers to an amount of fluid in the lungs that poses a health risk to the patient (e.g., in terms of difficulty breathing, and/or reduced oxygen saturation), and/or requires treatment. It is noted that some excess lung fluid may be tolerated. The amount of fluid that is considered as clinically significant may vary, for example, by patient and/or by treating physician, and/or according to the type of fluid (e.g., source, transudate, exudates, mostly water, blood, pus). The threshold separating between clinically significant and non-clinically significant lung fluid may be set, for example, manually by a user (e.g., via a graphical user interface), obtained from a stored system parameter, and/or automatically computed by code (e.g., based on an analysis of the patient health record.

As used herein, the terms electrode and sensor are sometimes interchangeable.

Figure 2:
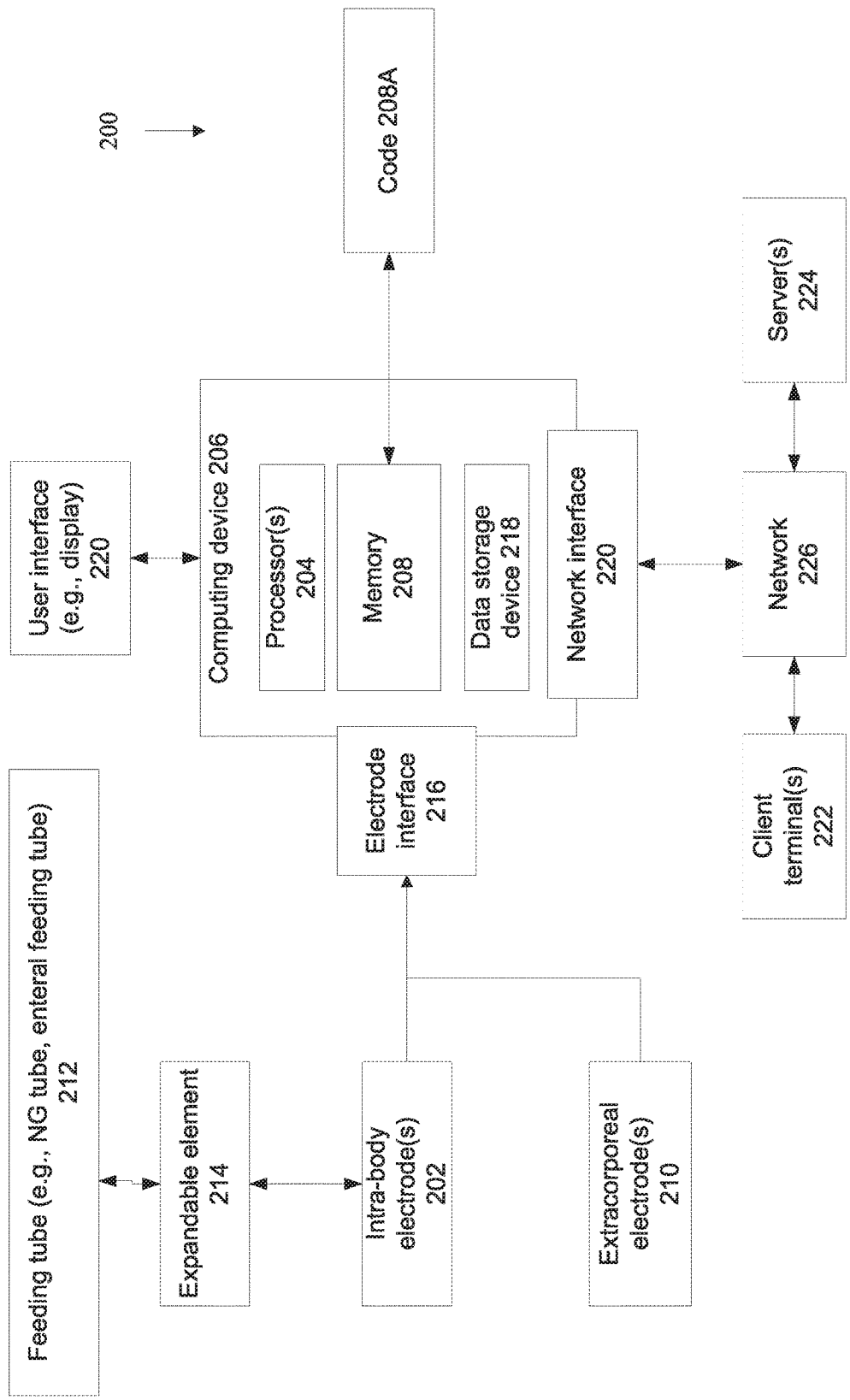
FIG. 2 is a schematic of components of a system for sensing lung fluid of a target patient based on at least one intra-body electrode positioned within the esophagus and/or stomach of a target patient, in accordance with some embodiments of the present invention.

Reference is now made to FIG. 1, which is a flowchart of a method for sensing lung fluid of a target patient based on at least one electrode positioned within the esophagus and/or stomach of a target patient, in accordance with some embodiments of the present invention. Reference is also made to FIG. 2, which is a schematic of components of a system 200 for sensing lung fluid of a target patient based on at least one intra-body electrode 202 positioned within the esophagus and/or stomach of a target patient, in accordance with some embodiments of the present invention. One or more of the acts of the method described with reference to FIG. 1 may be implemented by components of system 200, as described herein, for example, by a processor(s) 204 of a computing device 206 executing code instructions 208A stored in a memory 208 (also referred to herein as a data storage device).

Computing device 206 receives electrical signals outputted by intra-body electrode(s) 202 and/or extracorporeal electrode(s) 210. Intra-body electrode(s) 202 are positioned on a feeding tube 212. At least one intra-body electrode 202 is located on the distal end of feeding tube 212, such that when feeding tube 212 is inserted into the esophagus of the target patient, intra-body electrode 202 is positioned in proximity to the lower esophageal sphincter (LES), for example, above the LES within the esophagus, or within the stomach (e.g., the antrum of the stomach).

Intra-body electrode(s) 202 may be associated with an expandable element 214 located on the distal end of feeding tube 212, for example, an inflatable balloon, an expanding mesh made out of memory metal, and/or a sponge. Expandable element 214 is expanded (e.g., inflated, self-expanding) when feeding tube 212 is positioned within the esophagus, creating a contact (optionally by applying a force) between intra-body electrode(s) 202 and the inner wall of the esophagus and/or stomach. The contact transmits electrical signals and/or current between intra-body electrode(s) 202 and the nearby tissue.

Optionally feeding tube 212 is implemented as an enteral feeding tube for feeding the patient. The enteral feeding tube is positioned within the gastrointestinal system of the patient, for example, within the stomach, duodenum, or upper small intestine. Patients being enterally fed may be monitored for accumulation of clinically significant lung fluid without requiring insertion of an additional probe, since the enteral feeding tube is already necessary to feed the patient. Intra-body electrode(s) 202 is positioned in proximity to the LES when the enteral feeding tube is in the proper feeding position. The enteral feeding tube provides an additional function of monitoring the patient for accumulation of clinically significant lung fluid.

Alternatively or additionally, feeding tube 212 is implemented as a nasogastric (NG) tube for evacuation of contents from the stomach. The NG tube is positioned within the gastrointestinal system of the patient, for example, within the stomach, duodenum, or upper small intestine. Patients having their stomach contents being drained and/or stomach maintained in a drained state may be monitored for accumulation of clinically significant lung fluid without requiring insertion of an additional probe, since the NG tube is already necessary to treat the patient. Intra-body electrode(s) 202 is positioned in proximity to the LES when the NG tube is in the proper stomach content draining position. The NG tube provides an additional function of monitoring the patient for accumulation of clinically significant lung fluid.

Intra-body electrode(s) 202 may be associated with an attachment mechanism, optionally a clip-on attachment, for example, a clip, a C-shaped clip, for connection to existing off-the-shelf feeding tubes 212. Alternatively, enteral feeding tubes are manufactured integrally with intra-body electrode(s) 202, for example, intra-body electrode(s) 202 are glue, crimped, injection molded, and/or build-in to the outer surface of the enteral feeding tube.

Alternatively, feeding tube 212 is implemented as an elongated catheter. The catheter may include one or more lumens that house wires for transmission of signals between intra-body electrode(s) 202 and computing device 206.

Extracorporeal electrode 210 may be implemented as a pad electrode. Extracorporeal electrode 210 is designed for placement externally to the skin of the target patient. Extracorporeal electrode 210 may include a sticky portion for sticking to the surface of the skin. Extracorporeal electrode 210 may be positioned over the surface of the skin, with an optional conduction medium (e.g., gel) providing electrical conductivity between extracorporeal electrode 210 and the skin.

Electrodes 202 and/or 210 may include one or more electrodes that apply a currently and/or measure an applied current. Optionally, an electrode component of electrode(s) 202 and/or 210 applies the current and a electrode component of electrode(s) 202 and/or 210 senses the applied current. Alternatively or additionally, a single electrode may perform the functions of applying the current and sensing the current. Optionally, the extracorporeal (i.e., skin) electrodes may be mounted on both sides of the skin of the patient and/or around the thorax, enabling the independent measurement of lung fluid for each lung.

Computing device 206 may receive the outputs of electrodes 202 and/or 210 via one or more electrode interfaces 216, for example, a network interface, a wire connection, a wireless connection, a local bus, other physical interface implementations, and/or virtual interfaces (e.g., software interface, application programming interface (API), software development kit (SDK)).

Electrodes 202 and/or 210 may connect wirelessly and/or via wires with electrode interface 216 of computing device 206.

Computing device 206 may be implemented as, for example, a standalone integral unit, a virtual machine, a client terminal, a server, a computing cloud, a mobile device, a desktop computer, a thin client, a Smartphone, a Tablet computer, a laptop computer, a wearable computer, glasses computer, and a watch computer. Computing device 206 may be implemented as a customized unit that include locally stored software and/or hardware that perform one or more of the acts described with reference to FIG. 1. Alternatively or additionally, computing device 206 may be implemented as code instructions loaded on an existing computing device. Alternatively or additionally, computing device 206 may be implemented as hardware and/or code instructions (e.g., an accelerator card) installed and/or integrated within an existing computing device.

Processor(s) 204 of computing device 206 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 204 may include one or more processors (homogenous or heterogeneous), which may be arranged for parallel processing, as clusters and/or as one or more multi core processing units.

Memory 208 stores code instructions executable by processor(s) 204. Memory 208 is implemented as, for example, a random access memory (RAM), virtual memory, read-only memory (ROM), and/or a storage device, for example, non-volatile memory, magnetic media, semiconductor memory devices, hard drive, removable storage, and optical media (e.g., DVD, CD-ROM). Memory 208 stores code instructions 208A that implement one or more acts of the method described with reference to FIG. 1. Alternatively or additionally, one or more acts of the method described with reference to FIG. 1 are implemented in hardware.

As used herein, the term code instructions may refer to a software implementation in which one or more hardware processors execute code stored in a memory, and/or a hardware implementation. For example, computing device 206 may include a circuit designed for impedance estimation, for example, AFE4300 available from Texas Instruments.

Computing device 206 may include a data storage device 218 for storing data, for example, a history of computed impedance values and/or estimated amounts of lung fluid. Data storage device 218 may be implemented as, for example, a memory, a local hard-drive, a removable storage unit, an optical disk, a virtual memory, a storage device, and/or as a remote server and/or computing cloud (e.g., accessed via a network connection).

Computing device 206 includes and/or is in communication with a user interface 220 that includes a mechanism for a user to enter data (e.g., patient information) and/or view presented data (e.g., estimated amount of lung fluid, trend of amount of lung fluid). Exemplary user interfaces 220 include, for example, one or more of, a touchscreen, a display, a keyboard, a mouse, and voice activated software using speakers and microphone. External devices, such as client terminals 222 and/or server(s) communicating with computing device 206 over a network may serve as user interface 220, for example, a smartphone running an application may establish communication (e.g., cellular, network, short range wireless) with computing device 206 over network 226 using a communication interface (e.g., network interface, cellular interface, short range wireless network interface). The user may enter data and/or view data on the display of the smartphone, optionally via a graphical user interface (GUI) application.

Computing device 206 may be in communication with client terminal(s) 222 and/or server(s) 224 over network 226 via a network interface 228. Network interface 228 may be implemented as, for example, a network interface card, a hardware interface card, a wireless interface, a physical interface for connecting to a cable, a virtual interface implemented in software, communication software providing higher layers of connectivity, and/or other implementations.

Client terminal(s) 222 and/or server(s) 224 may receive indications generated by computing device 206, for example, currently computed estimate of amount of lung fluid, computed trend of amount of lung fluid, warning that amount of lung fluid is clinically significant, and/or a prediction warning that the trend of the amount of lung fluid is indicating of an impending accumulation of a clinically significant amount of lung fluid. Exemplary client terminal(s) 222 include: a mobile device, a smartphone, a tablet computer, a remotely located personal computer, a glasses computer, and a watch computer. Exemplary server(s) 224 include: a hospital medical record server (e.g., the transmitted data may be automatically logged into the patient electronic medical record), and/or a remote monitoring station (e.g., nurses station that monitors multiple patients on the ward).

Referring now back to act 102 of FIG. 1, the intra-body electrode(s) 202 are positioned within the esophagus of the patient, and/or within the stomach of the patient. Intra-body electrode(s) 202 are positioned by placement of feeding tube 212 within the esophagus and/or stomach of the patient.

Intra-body electrode(s) 202 may be first connected to an off-the-shelf feeding tube, for example, by a C-shaped clamp connector of intra-body electrode(s) 202 designed to snap tightly to a distal end of feeding tube 212. Alternatively, intra-body electrode(s) 202 are pre-connected to feeding tube 212.

Optionally, intra-body electrode(s) 202 located a defined location(s) along the distal end portion of feeding tube 212 and are positioned correctly within the patient when feeding tube 212 is positioned within esophagus and/or stomach according to the intended purpose of feeding tube 212. For example, when feeding tube 212 is implemented as a nasogastric (NG) tube for evacuation of stomach contents, intra-body electrode(s) 202 located at the distal end of the NG tube are correctly positioned when NG tube is correctly positioned for the evacuation of stomach contents. In another example, when feeding tube 212 is implemented as a enteral feeding tube (inserted into the patient via the nose, the mouth, and/or a surgically created orifice) for enteral feeding of the patient, intra-body electrode(s) 202 located at the distal end of the feeding tube are positioned correctly when the feeding tube is correctly positioned for feeding of the patient. When feeding tube 212 is designed as a catheter, the catheter may be designed to correctly position intra-body electrode(s) 202 within the esophagus, for example, by a defined length of the catheter, and/or a shape of the catheter designed to stop at the LES.

Feeding tube 212 may include multiple intra-body electrodes 212 spaced apart from one another, and located along the length of feeding tube 212. The multiple intra-body electrodes 212 may generate a tomographical impedance map of fluid in the lung according to their respective locations.

At least one of intra-body electrodes 202 is located in proximity to the LES, for example, contacting the LES, or less than about 1 centimeter (cm), or 3 cm, or 5 cm, or 10 cm, or other values. The intra-body electrode 202 may be located above the LES (within the esophagus), or below the LES (e.g., within the stomach, optionally the antrum).

The location of intra-body electrodes 202 in proximity to the LES positions intra-body electrodes 202 below the level of the heart, and/or in proximity to the base of the lung(s) where fluid begins to accumulate. The impedance measurement obtained by the intra-body electrodes 202 in proximity to the LES avoids or reduces current through the heart. Alternatively or additionally, the impedance measurement obtained by the intra-body electrodes 202 in proximity to the LES is indicative of fluid at the base of the lung(s), where the fluid may begin to accumulate, to obtain an early indication of clinically significant accumulation of lung fluid.

Intra-body electrode(s) 202 are placed in contact with the inner wall of the esophagus and/or stomach. Optionally, expandable element 214 applies a force to contact intra-body electrode(s) 202 with the inner wall of the esophagus and/or stomach, for example, by expanding a balloon, and/or self-expansion of memory metal.

Intra-body electrode(s) 202 may be positioned below the axial plane of the heart.

At 104, extracorporeal electrode(s) 210 are positioned. Extracorporeal electrode(s) 210 may be stuck to the skin of the patient, for example, by a sticky pad and/or tape. A conductive gel may be applied to improve electrical coupling between extracorporeal electrode(s) 210 and the skin of the target patient.

Exemplary locations for positioning of extracorporeal electrode(s) 210 include: along the lower rib or slightly above the lower rib (e.g., within about 5-10 centimeter), at the axillary line (e.g., anterior, mid, posterior), mid clavicular line, and one the back in proximity to the spine and/or between the spine and posterior axillary line.

Extracorporeal electrode(s) 210 may be positioned below the axial plane of the heart.

The location of extracorporeal electrode(s) 210 may impact the type of lung fluid that is being monitored. Optionally, one or more extracorporeal electrode(s) are positioned on the skin of the patient corresponding to one or more lobes of the lungs, optionally the base of the lungs. The lobe(s) of the lung(s) may be monitored for pulmonary edema, which accumulates within the alveoli of the lung itself, and may accumulate per lobe. For example, the extracorporeal electrode(s) may be placed on the chest for monitoring the anterior lobe(s) and/or the right middle lube, and/or placed on the back for monitoring the posterior lobe(s). Alternatively or additionally, one or more extracorporeal electrode(s) are positioned on the skin of the patient corresponding to the base of the lung, for example, for monitoring for pulmonary effusion which develops within the pleural space and tends to sink to the lower part of the pleural space around the base of the lung.

Pulmonary edema may be differentiated from pleural effusion according to the impedance values measured by multiple extracorporeal electrode(s) at different locations. For example, impedance values that are relatively lower at specific electrodes at positions corresponding to specific lobes may be indicative of pulmonary edema, whereas impedance values that are relatively lower at the base of the lung but relatively constant elsewhere may be indicative of pulmonary effusion.

Extracorporeal electrode(s) 210 may be positioned on the skin of the patient at a location corresponding to the costophrenic angle (e.g., for monitoring for pulmonary effusion). Extracorporeal electrode(s) 210 may be positioned as far away from the heart as possible, but at the same time at a location(s) corresponding to the lung(s).

Extracorporeal electrodes 210 may be positioned for parallel monitoring of both left and right lungs for accumulation of clinically significant amount of fluid.

As discussed herein, the locations of intra-body electrode(s) 202 in proximity to the LES and the location of extracorporeal electrode(s) 210 prevent applied AC from reaching the heart, and/or reduce the portion of the AC that reaches the heart to safe levels. Electrodes may be mounted on the skin around the torso. The exact location and/or number of electrodes may be determined, for example, by the physician depending on the patient's condition.

Figure 3:
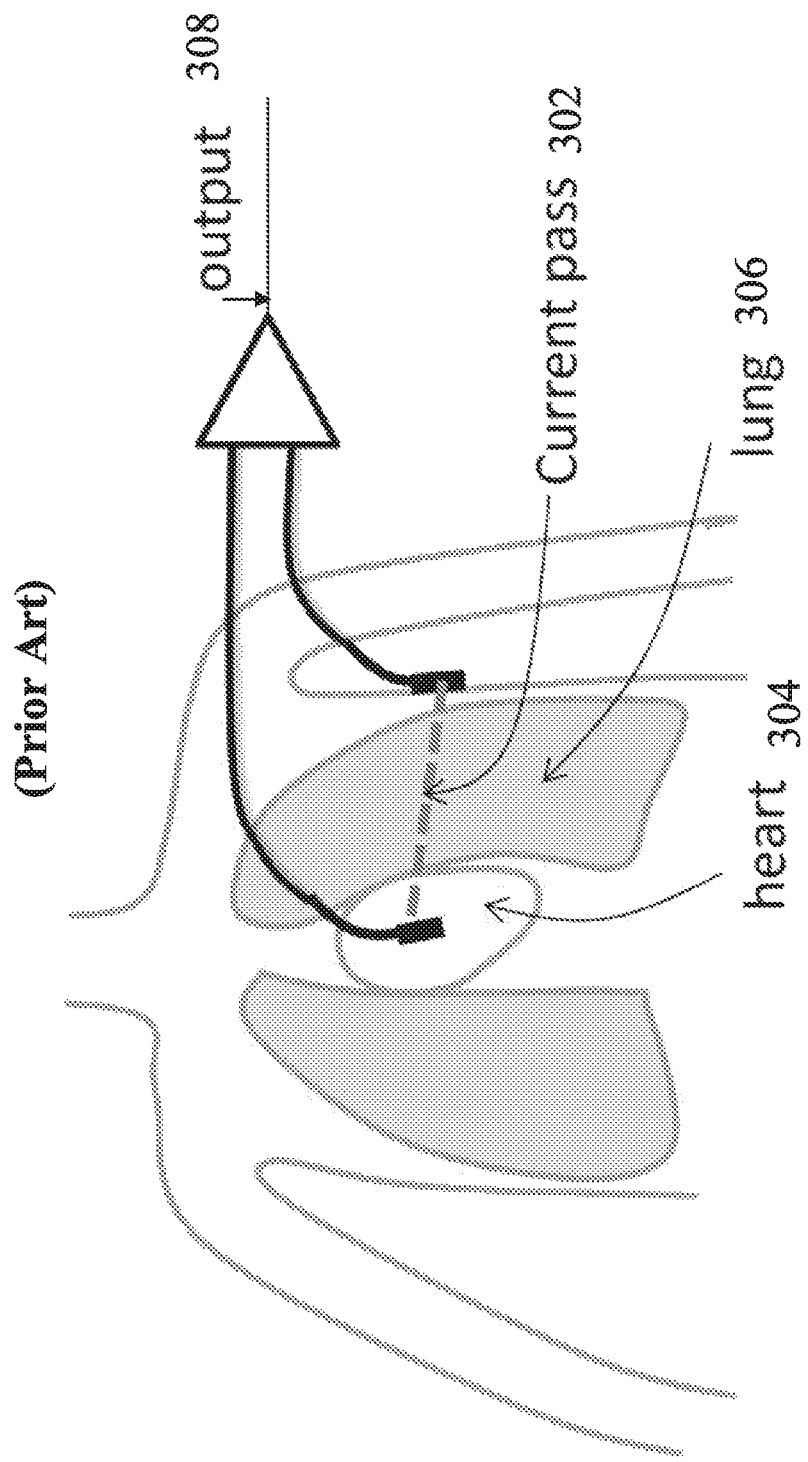
FIG. 3 is a schematic depicting a dangerous set-up of measuring lung fluid based on other proposed approaches, to illustrate the safe set-up according to some embodiments of the present invention.

Reference is now made to FIG. 3, which is a schematic depicting a dangerous set-up of measuring lung fluid based on other proposed approaches, to illustrate the safe set-up according to some embodiments of the present invention. Other proposed approaches are based on generating a current 302 that passes through a heart 304 of the target patient for sensing fluid within a lung 306 of the patient. Current 302 passing through heart 304 greatly increases the risk of arrhythmias, and may damage and/or interfere with devices implanted within heart 304, for example, a pacemaker. Current 302 passes between one electrode positioned within heart 304 and another electrode positioned in proximity to lung 306, resulting in current 302 travelling through both lung 306 and heart 304 to generate output 308. Output 308 is analyzed to sense fluid within lung 306. It is noted that the analysis of output 308 includes additional irrelevant data of heart 304, and therefore is less accurate in sensing fluid within lung 306.

Figure 4:
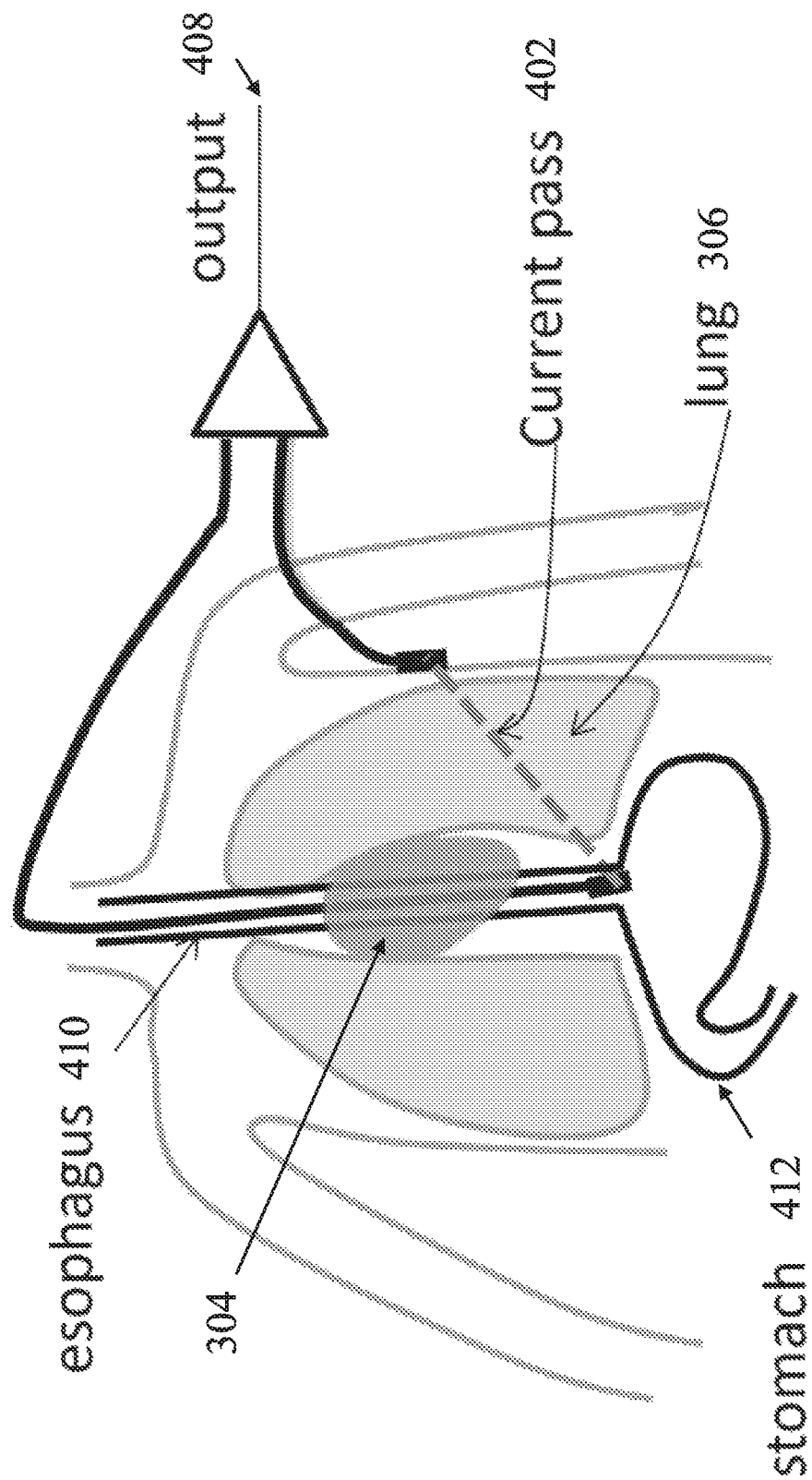
FIG. 4 is a schematic depicting a safe set-up of measuring lung fluid based on an alternating current passing through the lung(s) while avoiding passing through the heart, in accordance with some embodiments of the present invention.

Reference is now made to FIG. 4, which is a schematic depicting a safe set-up of measuring lung fluid in lung 306 based on current 402 passing through lung 306 while avoiding passing through heart 304, in accordance with some embodiments of the present invention. The set-up described with reference to FIG. 4, based on embodiments described herein, is in contrast to the set-up according to other approach as described with reference to FIG. 3. It is noted that some current may pass through heart 304, however such current is weak and unable to trigger arrhythmias and/or interfere with devices implanted in heart 304. Current 402 passes through lung 306 while avoiding heart 304 based on the positioning of intrabody electrode(s) at the distal end portion of esophagus 410 (e.g., in proximity to the LES) and/or at the entrance of stomach 412 (e.g., within the antrum), and the positioning of extracorporeal electrode(s) on the surface of the patient's skin in proximity to lung 306. The fluid in lung 306 is sensed based on an analysis of output 408 indicative of the impedance of the current 402 passing through lung 306.

At 106, one or more alternating current (AC) are applied. AC currents may be applied at different frequencies, to compute a set of impedance values measured at each respective different frequency. For example, a defined pattern of AC frequencies may be applied sequentially, for example, a single frequency during a single time interval.

The accumulated results may be presented to the physician, optionally based on a Cole-Cole type diagram.

The following are some examples of set-ups for applying the AC current and performing a measurement, optionally of voltage:

When the AC current is applied between intra-body electrode 202 and the extra corporal electrode 210. Voltage is measured by between intra-body electrode 202 and extracorporeal electrode 210 of one or both lungs. Voltage of both lungs may be measured simultaneously. In implementation of multiple intra-body electrodes 202 and/or multiple extracorporeal electrodes 210, different activation patterns of a single intra-body electrode 202 and/or a single extracorporeal electrode 210 may be applied.

At 108, output is received from extracorporeal electrode(s) 210 and/or intra-body electrode(s) 202. Optionally, the output includes an indication of a measured voltage (e.g., voltage drop) between extracorporeal electrode(s) 210 and intra-body electrode(s) 202. It is noted that extracorporeal electrode(s) 210 and/or intra-body electrode(s) 202 may act as sensors. Alternatively, the sensing feature is performed by a sensor component of extracorporeal electrode(s) 210 and/or intra-body electrode(s) 202.

Optionally, the output is sensed while the alternating current is applied.

At 110, impedance is computed. Optionally, the impedance is computed for each lung, or for one lung. The impedance may be computed according to the applied alternating current and the measured voltage.

In terms of mathematical representation, the applied alternating current is denoted as $$I_0 e^{i\omega t}$$

where $I_0$ denotes the amplitude of the current and co denotes the frequency.

The equivalent impedance across the tissues, including the lung and any fluid therein, between intra-body electrode 202 and extracorporeal electrode 210 may be mathematically represented based on the following relationship:

$$Z_L = V_0 e^{i(\omega t - \theta)} / I_0 e^{i\omega t}$$

Where d $V_0 e^{i(\omega t-\theta)}$ measured between intrabody electrode 202 and extracorporeal electrode 210.

The current may be applied by an AC microampere source 610.

The voltage may be measured by an instrumentation amplifier 612.

The impedance may be computed according to the measured voltage and applied current based on the above described relationship by computing device 206 (e.g., by hardware processor(s) 204) executing code 208A stored in memory 208). The estimated amount of fluid and/or the computed impedance may be presented within a GUI (e.g., as a real-time value, as a graph indicative of a trend over a recent time interval) on a display 220.

Figure 5:
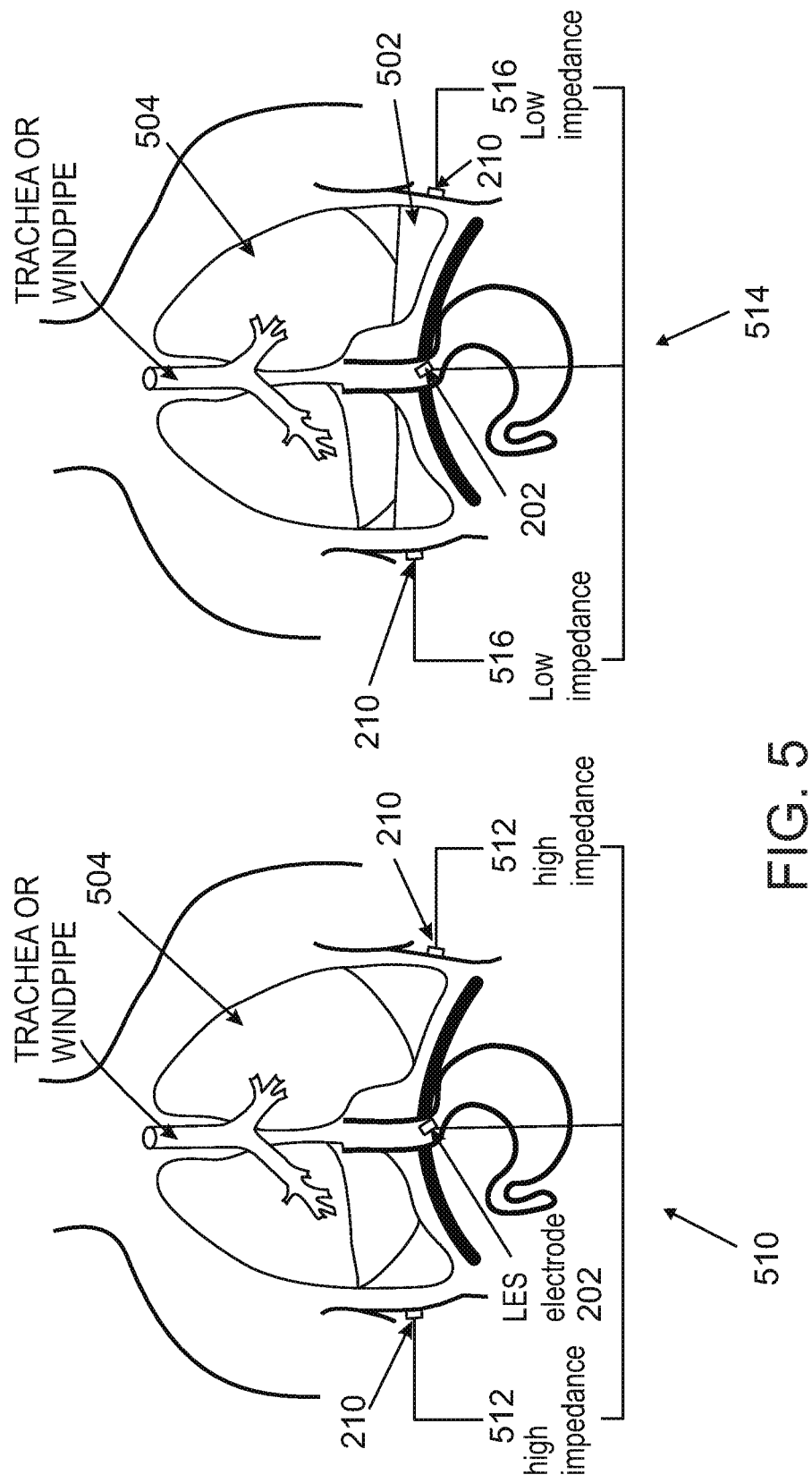
FIG. 5 is a schematic depicting an exemplary positioning of intra-body electrode(s) and extracorporeal electrode(s) for sensing fluid in one or more lungs of a target individual, in accordance with some embodiments of the present invention.

Reference is now made to FIG. 5, which is a schematic depicting an exemplary positioning of intra-body electrode 202 and extracorporeal electrode(s) 210 for sensing fluid 502 in one or more lungs 504 of a target individual, in accordance with some embodiments of the present invention.

Intra-body electrode 202 may be positioned within the esophagus, above the LES, and/or approximately corresponding to the location of the diaphragm. One or more extracorporeal electrode(s) 210 are associated with each lung 504. Extracorporeal electrode(s) 210 are positioned on the skin of the patient in proximity to the lung 504 lying beneath the skin. Extracorporeal electrode(s) 210 may be positioned in proximity to the base of each lung 504, since fluid 502 accumulates starting from the base of each lung 504.

Schematic 510 depicts the state of lung(s) 504 of the patient without any (or clinically insignificant amount of) excess fluid. Impedance values measured between intra-body electrode 202 and extracorporeal electrode(s) 210 are relatively high 512.

Schematic 514 depicts the state of lung(s) 504 of the patient with a clinically significant amount of excess fluid 502. Impedance values measured between intra-body electrode 202 and extracorporeal electrode(s) 210 are relatively low 516.

Figure 6:
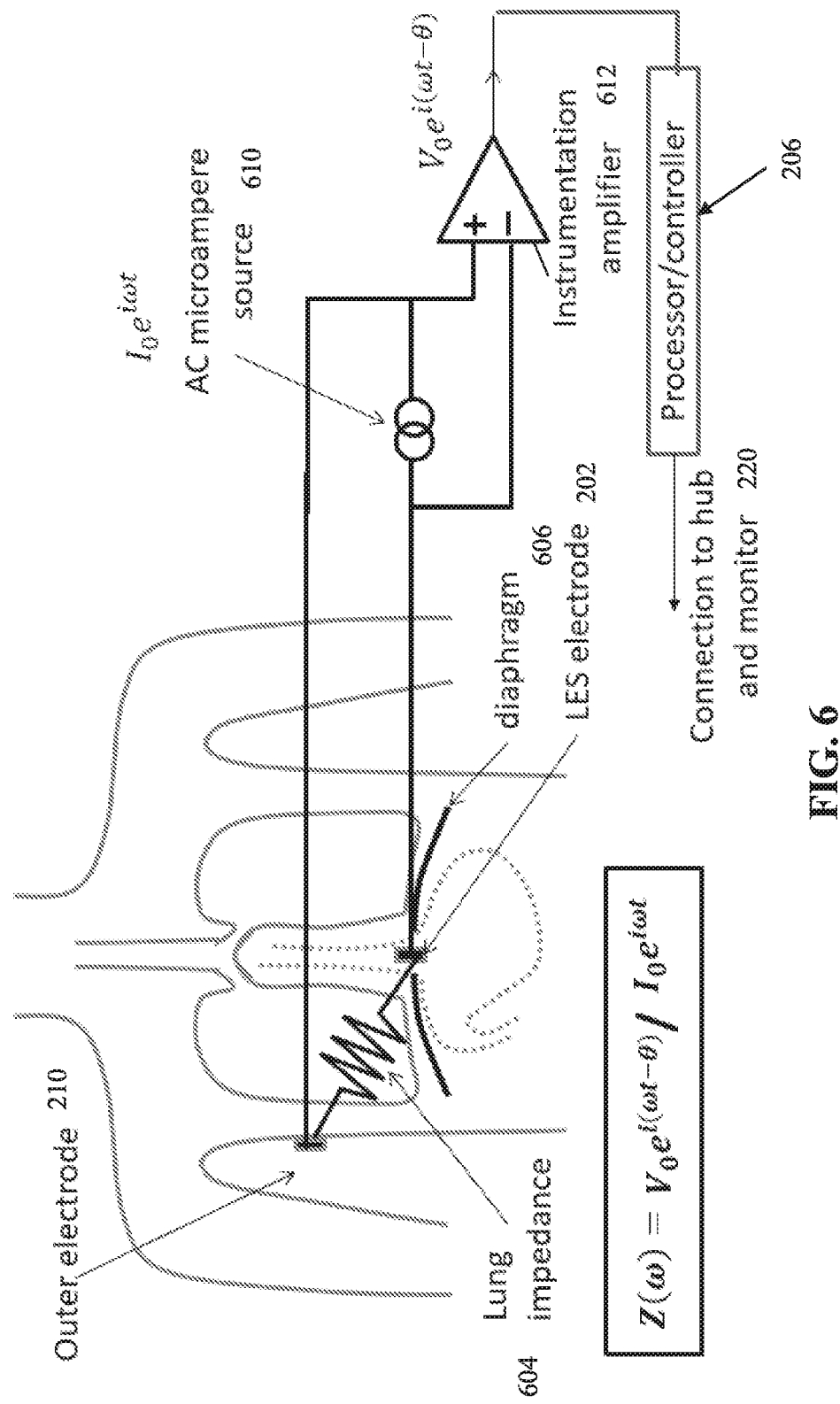
FIG. 6 is a schematic depicting an electrical setup for measurement of impedance across a lung of target individual for sensing fluid within the lung, in accordance with some embodiments of the present invention.

Reference is now made to FIG. 6, which is a schematic depicting an electrical setup for measurement of impedance across a lung of target individual for sensing fluid within the lung, in accordance with some embodiments of the present invention. Lung impedance is denoted as 604. An alternating current (AC) is applied to the lung via intra-body electrode(s) 202 and sensed by extracorporeal electrode(s) 210. Intrabody electrode 202 is located at a height corresponding to a diaphragm 606 and/or above the LES. Alternatively or additionally, AC current is applied by extracorporeal electrode(s) 210 and sensed by intra-body electrode(s) 202. Alternatively or additionally, AC current is applied by both extracorporeal electrode(s) 210 and intra-body electrode(s) 202 and sensed by both extracorporeal electrode(s) 210 and sensed by intra-body electrode(s) 202, for example, applied by an electrode component of extracorporeal electrode 210 and sensed by a sensor component of extracorporeal electrode 210.

Figure 7:
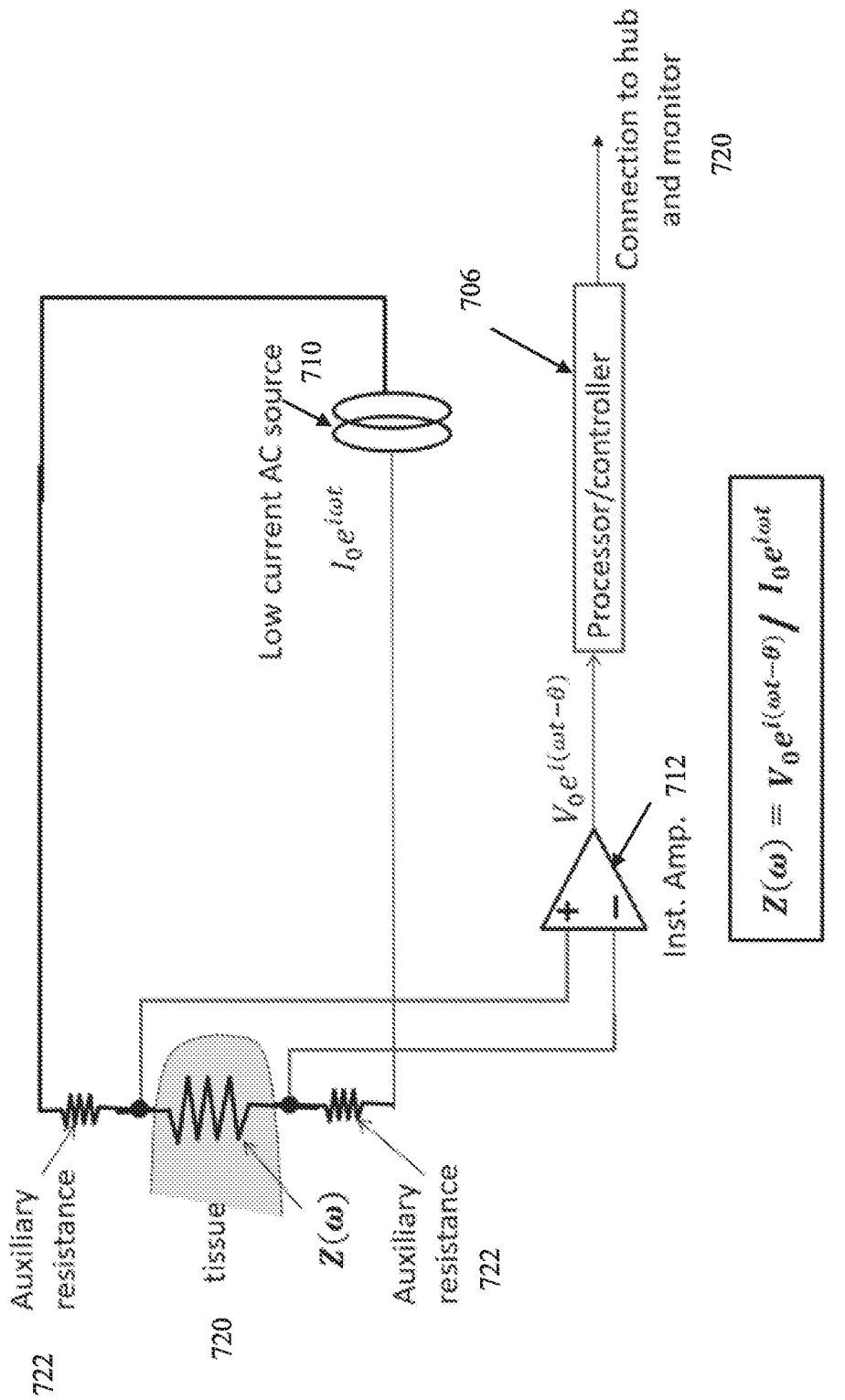
FIG. 7 is a schematic depicting an abstract representation of the electrical setup for measurement of impedance across a lung of target individual for sensing fluid within the lung, in accordance with some embodiments of the present invention.

Reference is now made to FIG. 7, which is a schematic depicting an abstract representation of the electrical setup for measurement of impedance across a lung of target individual for sensing fluid within the lung, in accordance with some embodiments of the present invention. A low current AC source 710 applies the AC to a lung tissue 720 and other nearby tissues that include auxiliary resistance 722. An instrumentation amplifier 712 measures the voltage across lung tissue 720, between the intra-body electrode(s) and the extracorporeal electrode(s). A processor(s) and/or controller 706 (e.g., computing device 206 described with reference to FIG. 2) computes the impedance across lung tissue 720 based on the AC applied by source 710 and the voltage measured by instrumentation amplifier 712. The computed impedance and/or estimate of the corresponding amount of lung fluid is provided to a hub and/or or presentation on monitor (e.g., within a GUI) 720.

Figure 8:
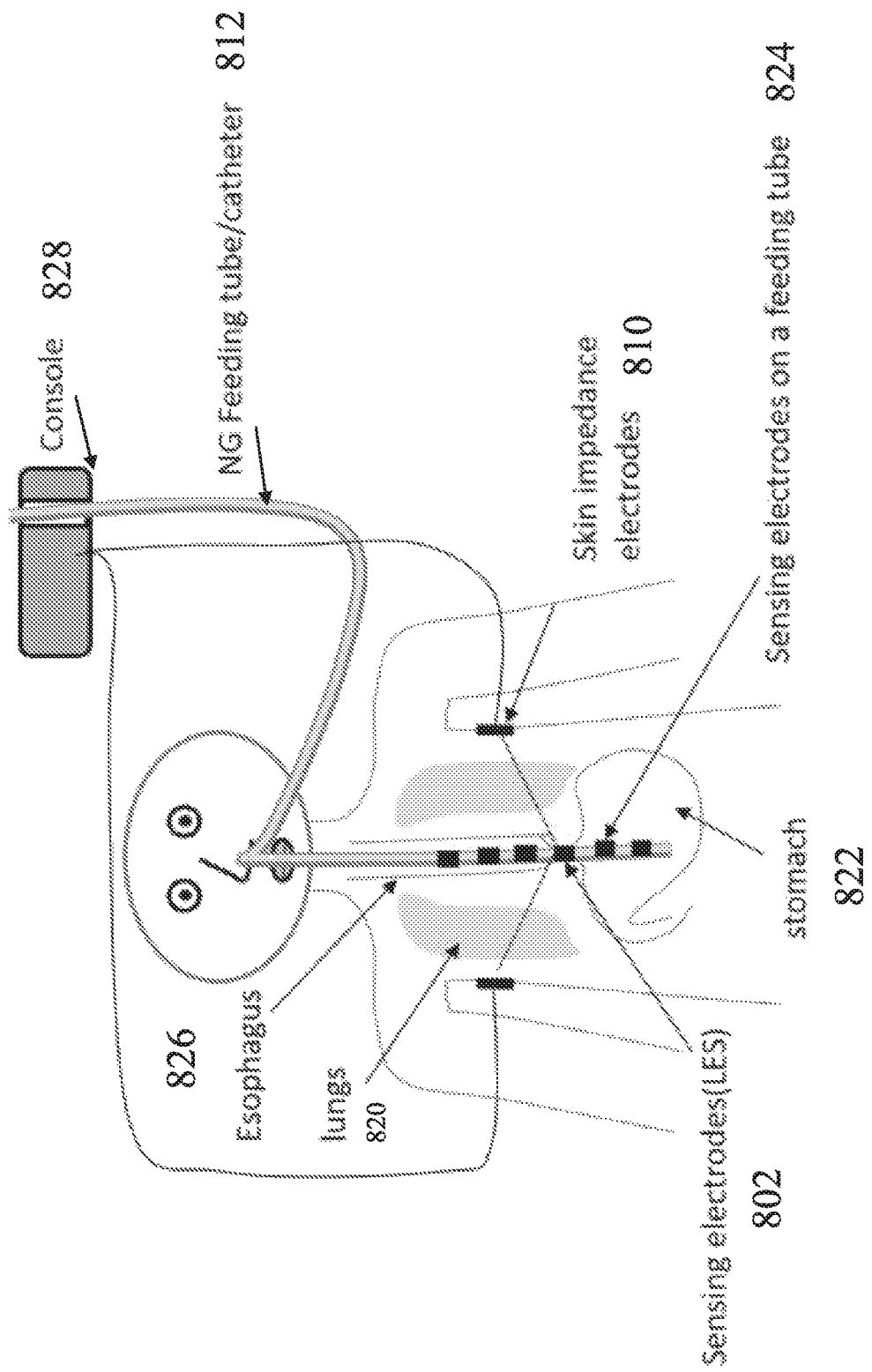
FIG. 8 is a schematic of an environment set-up for sensing fluid within a lung(s) of a target patient based on an intra-body electrode(s) positioned along a feeding tube located within an esophagus of a target individual, in accordance with some embodiments of the present invention.

Reference is now made to FIG. 8, which is a schematic of an environment set-up for sensing fluid within a lung(s) 820 of a target patient based on an intra-body electrode(s) 802 positioned along a feeding tube 812 located within an esophagus 826 of a target individual, in accordance with some embodiments of the present invention. At least one intra-body electrode 802 is located on feeding tube 812 at a location corresponding to the LES when feeding tube 812 is correctly positioned within esophagus 826 and a stomach 822 of the target individual. Additional electrodes 824 may be positioned along the length of feeding tube 812, above and/or below the location of intra-body electrode 802 located at the position corresponding to the LES. A console 828 (e.g., computing device) receives controls application of an alternative current to intra-body electrodes 802 and optionally other electrodes 824 located on feeding tube 812. Console 828 receives voltage measurements sensed by extracorporeal electrodes 810. Alternatively or additionally, console 828 applies AC via extra-corporeal electrodes 810 and receives voltage measurements performed by intra-body electrodes 802 and optionally electrodes 824. Console 828 computes the impedance across lung(s) 820 according to the applied AC and measured voltage(s). An indication of clinically significant or clinically insignificant or no fluid in lung(s) 820 may be generated accordingly, and optionally presented on a display within a GUI, for example, as a trend line.

Figure 9:
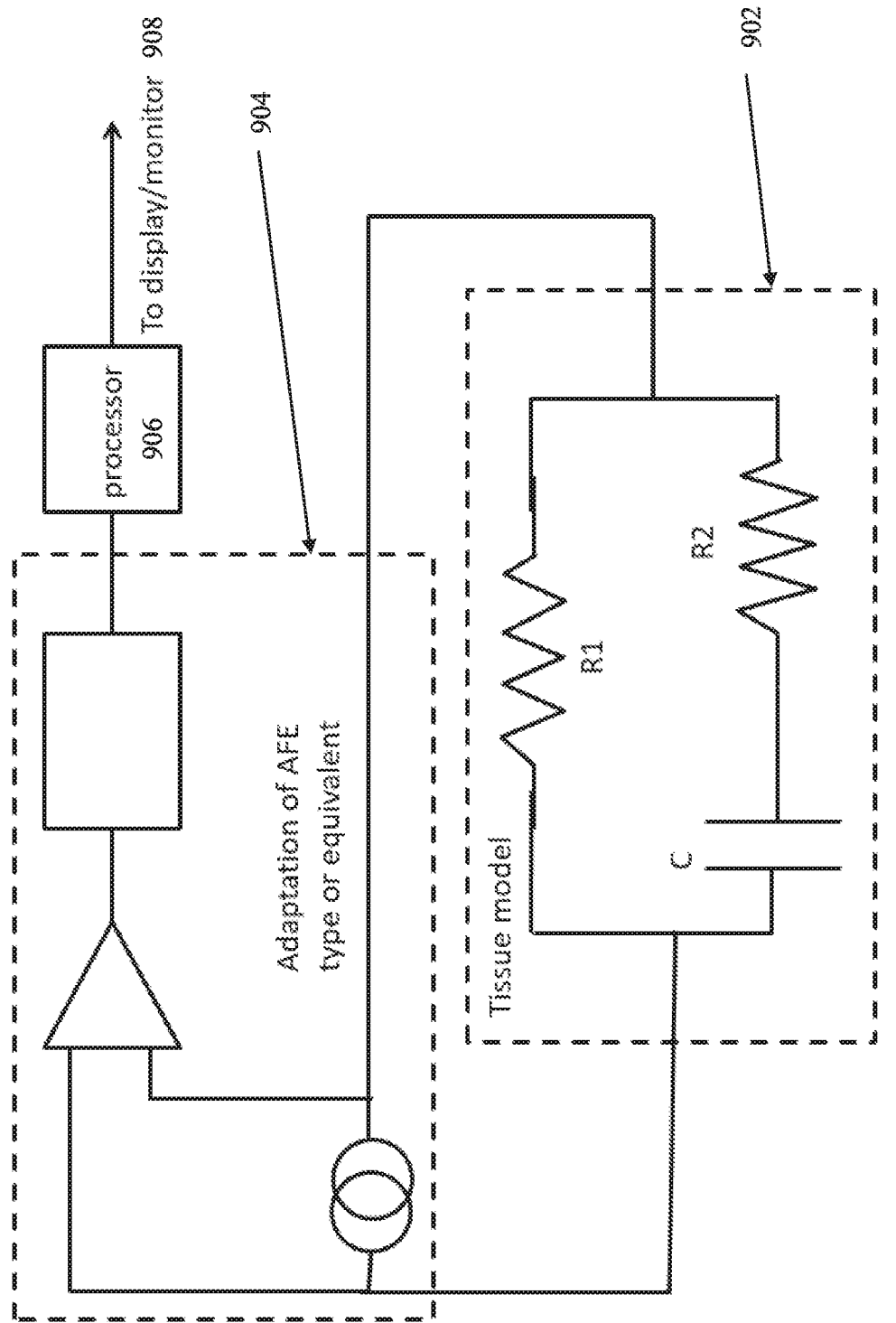
FIG. 9 is a schematic of an electronic measurement system for sensing fluid within one or more lungs of a patient based on at least one intra-body electrode positioned within the esophagus in proximity to the LES, in accordance with some embodiments of the present invention.

Reference is now made to FIG. 9, which is a schematic of an electronic measurement system for sensing fluid within one or more lungs of a patient based on at least one intra-body electrode positioned within the esophagus in proximity to the LES, in accordance with some embodiments of the present invention. Component 902 represents a model of the tissues between the intra-body electrode positioned within the esophagus in proximity to the LES, and an extracorporeal electrode. The tissues mostly include the lung, and other associated tissues, for example, bone and muscle. The tissues are modeled as including one or more capacitors and one or more resistors. Component 904 represents circuitry that generates AC currents and receives measurements of voltage from the electrodes, as described with reference to FIGS. 6 and/or 7. Processor(s) 906 computes the impedance according to the generated AC and measured voltage, as described herein. An indication of the impedance and/or sensed amount of lung fluid is provided for display 908, for example, within a GUI on a display.

At 112, an indication of an estimated amount of lung fluid (e.g., absolute amount, and/or change relative to a baseline) in one or both lungs of the patient is computed. The indication is computed based on the measured impedance values. Optionally, the computed impedance value(s) is mapped to the estimated amount of lung fluid.

The amount of lung fluid change may be independently estimated for each lung, according to impedance values computed based on the extracorporeal electrodes applied to the skin corresponding to teach lung.

The amount of lung fluid change may be estimated according to an initial baseline measurement performed at the start of the monitoring process.

The amount of lung fluid change may be estimated as a relative comparison between impedance values measured for the two lungs. The change in the lung fluid for each lung may be compared, for example, the impedance change of the left lung relative to baseline as a ratio of the impedance change of the right lung relative to baseline. The comparison between the two lungs may be help to differentiate between lung fluid processes that affect both lungs equally from lung fluid processes that affect only one lobe or only one lung (or affect one lobe or lung more than the others).

The computed impedance value may be mapped to a classification category of clinically significant amount of lung fluid, or clinically insignificant amount of lung fluid (which may include the absence of lung fluid). Alternatively or additionally, the computed impedance value is mapped to a relative amount of lung fluid relative to a threshold that separates between clinically significant and clinically insignificant amount of lung fluid, for example, indicative of severity. Alternatively or additionally, the computed impedance value is mapped to an estimated amount of lung fluid.

The computed impedance value may be mapped to an impedance score. The impedance score is relative to the threshold differentiating between clinically significant and clinically insignificant amount of lung fluid. The impedance score includes a value and an associated time stamp indicative of the time at which the impedance value is measured. The impedance score may be presented on a graph of impedance scores obtained over time, as described herein.

The mapping between the impedance value and the estimated amount of lung fluid may be performed based on empirical data collected from sampled individuals, for example, measurements of impedance values performed on sample individuals for which a manual indication of the amount of lung fluid is estimated (e.g., an absolute amount of lung fluid which may be measured for example based on a thoracentesis in which the lung fluid is withdrawn into a calibrated container and the volume of the lung fluid is measured, and/or indication of clinically significant or clinically insignificant fluid determined based on clinical signs and/or symptoms). Alternatively or additionally, the mapping may be performed based on a mathematical model of dielectric properties of the tissues.

The mapping between the impedance value and the estimated amount of lung fluid may be performed, for example, based on a dataset of the empirically collected values (e.g., graph, look-up able), and/or a statistical classifier trained based on the data (e.g., neural network, linear regression, support vector machine).

One or more impedance values may be mapped to a single indication of the estimated amount of lung fluid. For example, multiple impedance values measured according to different frequencies of alternating currents may be aggregated and mapped to the single indication of estimated amount of lung fluid. The aggregation may include, for example, an average, and/or a weighted average computation of the impedance values.

Figure 10:
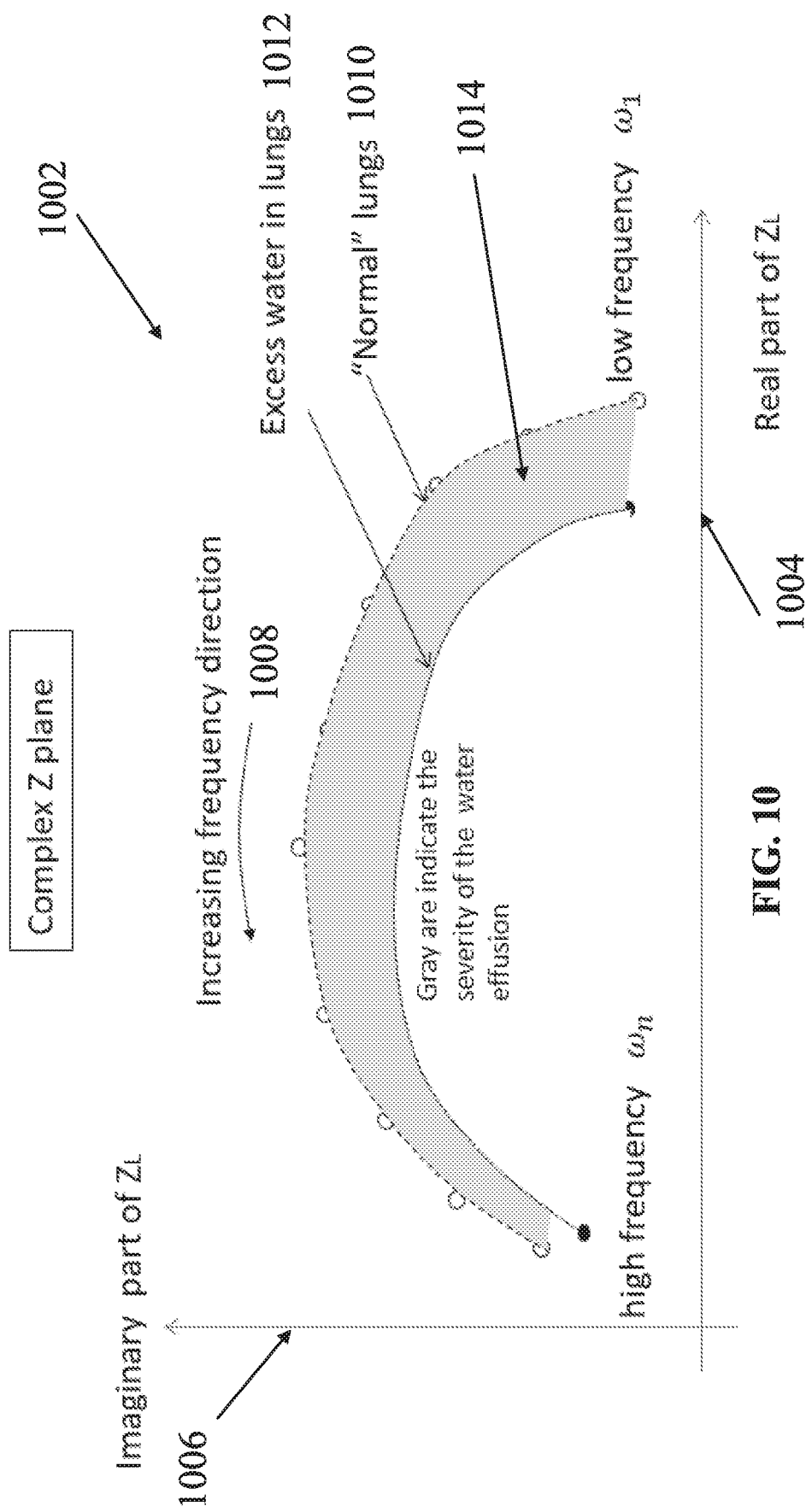
FIG. 10 is an exemplary graph for analyzing the computed impedance value(s) for determining an indication of a clinically significant amount of excess fluid in the lungs, in accordance with some embodiments of the present invention.

Reference is now made to FIG. 10, which is an exemplary graph 1002 for analyzing the computed impedance value(s) for determining an indication of a clinically significant amount of excess fluid in the lungs, in accordance with some embodiments of the present invention. Graph 1002 may be constructed based on, for example, impedance measurements obtained from one or more sample patients with varying degrees of lung fluid and associated medical evaluation of a reference amount of lung fluid. In another example, graph 1002 may be constructed based on a mathematical model, for example, computed according to the Cole-Cole equation as described with reference to Cole, Kenneth S, Robert H (1941). "*Dispersion and Absorption in Dielectrics: I—Alternating Current Characteristics*". *Journal of Chemical Physics*. 9: 341-351. In yet another example, parameters of the mathematical model are determined according to empirical data (impedance measurements on real patients).

It is noted that different graphs 1002 may be constructed for identification of different types of lung fluid, for example, transudative (i.e., mostly water), and different types of exudative (e.g., blood, pus, infectious materials, water with high percentage of other components). The type of lung fluid may be manually entered by a user (e.g., selected from a list presented on the GUI by clicking), and/or automatically determined by code instructions based on a sensor (e.g., based on an automated analysis of the lung fluid) and/or obtained from an electronic medical record (e.g., based on a laboratory result). Alternatively, a common graph 1002 is constructed based on the assumption that the differences between the types of lung fluid are not statistically significant in terms of detection of clinically significant amounts.

Graph 1002 plots complex impedance values as a point within a complex plane defined relative to a real component axis (x-axis) 1004 and an imaginary component axis (y-axis) 1006. Each impedance value may be mathematically represented as:

$$Z_L(\omega)=R_L(\omega)+iX_L(\omega)$$

Where $Z_L(\omega)$ denotes the impedance value, $R_L(\omega)$ denotes the real component, $X_L(\omega)$ denotes the imaginary component, and $\omega$ denotes the frequency of the applied alternating current.

It is noted that the frequency along the real component axis 1004 increases from right to left, as represented by arrow 1008.

The impedance value measured or the target patient is plotted on graph 1002, and analyzed as follows:

Impedance values plotted on graph 1002 that fall above a normal threshold (denoted by curve 1010) denote a lung without fluid, and/or with a normal amount of fluid, and/or with a clinically insignificant amount of fluid.

Impedance values plotted on graph 1002 that fall below a clinically significant amount of lung fluid threshold (denoted by curve 1012) denote a lung with a clinically significant amount of fluid.

Impedance values plotted on graph 1002 that fall within intermediate zone 1014 (bordered by curves 1010 and 1012) denote a lung that is at impending risk of accumulating a clinically significant amount of fluid.

Optionally, the lung impedance measurement and/or monitoring as described herein is based on an initial baseline measurement, followed by continuous and/or periodic updating with reference to the baseline measurement, for example, the baseline impedance is calibrated to zero, and additional measurements are calibrated with reference to the baseline value. The initial baseline impedance value and subsequence impedance values that are adjusted relative to the baseline may avoid the natural physiological variance distribution amongst the population.

When the impedance values fall within zone 1014, alerts may be generated (e.g., presented within a GUI on a display) indicating that the patient is at impending risk of accumulating a clinically significant amount of fluid. Indications of impedance values above threshold 1010 may be generated and presented within the GUI for monitoring the patient. Alerts of impedance values below threshold 1012 may be generated and presented within the GUI indicating that the patient has already accumulated a clinically significant amount of fluid.

Referring now back to FIG. 1, at 114, a trend line is computed according to the impedance values and/or impedance scores.

When the impedance values are represented as complex values, the complex values may be converted into an impedance score representation suitable for presentation, optionally as a point on a graph of impedance scores (e.g., along the y-axis) over time (e.g., along the x-axis). The impedance score representation may be computed as one of more of: the real component of the complex impedance value, a real representation of the imaginary component of the complex impedance value, and a real representation of the complex impedance value for example the length of a vector representation of the complex impedance value (e.g., square root of the squared real component and the squared imaginary component).

Each impedance score is associated with the time at which the respective impedance score is measured and/or computed.

The trend line is computed for the most recent impedance scores, for example, the most recent predefined number of impedance scores, over a recent predefined time interval, and/or according to a set of rules that defined events for computation of the trend line.

The trend line may be computed, for example, as a regression line fitted to the recent impedance score over a recent time interval according to a least square fit.

The trend line may be extended into the future for prediction likelihood of impending accumulation of clinically significant lung fluid. The likelihood of impending accumulation of clinically significant lung fluid may be predicted when the trend line crosses within a future predefined interval of time, a threshold differentiating between clinically significant amount of fluid and clinically insignificant amount of fluid.

The probability of the likelihood of impending accumulation of clinically significant amount of lung fluid may be computed, for example, as a number and/or a classification category (e.g., high risk, intermediate risk, low risk). The probably may be computed according to a correlation value indicative of fit of the trend line to the recent impedance scores, and/or the amount of time in the future when the trend line is predicted to reach the threshold. For example, a high R square value for fitting the trend line to the recent impedance scores and/or the trend line crossing the threshold in the near future are indicative of a high probability. A low R square value indicating a poor fit of the trend line, and/or an estimate of the trend line crossing the threshold in the far future are indicative of a low probability.

At 116, the indication of accumulation of lung fluid is presented on a display and/or transmitted as an alert (e.g., a phone call, an email, a pop-up message presented on a display).

The indication, optionally the impedance score, may be presented as a point on a graph, optionally within a graphical user interface (GUI) presented on the display. The graph includes a time axis (e.g., x-axis) indicative of the time at which the indication was obtained (e.g., impedance value measured), and an indication axis (e.g., y-axis) indicative of the value of the indication (e.g., value of the impedance score).

Points are plotted as the patient is monitored, optionally as impedance values are measured over time.

The computed trend line may be plotted within the graph on the GUI. The extension of the trend line may be presented within the graph. The future time at which the extension reaches and/or crosses the threshold may be indicated within the GUI. The computed probability of impending accumulation of clinically significant amount of fluid may be presented within the GUI.

Alternatively or additionally, the graph includes a baseline impedance value (e.g., impedance score) measured for the patient at a state determined to be clinically insignificant for lung fluid. The value of the impedance may be monitored by computing subsequent current impedance values. Change in the current impedance value relative to the baseline impedance value above a threshold may be indicative of accumulation (or close to accumulation) of clinically significant amount of lung fluid.

Optionally, an alert is generated when a set of rules is met, indicating impending accumulation of clinically significant amount of lung fluid, for example, when the computed probability of prediction of accumulation of clinically significant amount of fluid is above a threshold indicating high risk and/or when the trend line is heading in a direction towards a threshold denoting accumulation of clinically significant amount of fluid. Alternatively or additionally, the alert is generated when an estimated amount of lung fluid is sensed, for example, according to a threshold and/or range. The alert may be transmitted, for example, to a mobile device (e.g., of a health provider) and/or to a monitoring server (e.g., nurses' station), for example, as a pop-up box appearing on the screen with a text message indicating risk of impending accumulation of fluid, an email, a phone call, and/or a flashing light appearing within the GUI presenting the graph.

At 117, one or more additional features may be executed based on the computed impedance. The same electrodes and/or tube located within the esophagus may perform one or more additional features, in addition to the estimation of the amount of lung fluid. The additional features may be executed in parallel to the estimation of the amount of lung fluid, and/or sequentially in reference to the estimation of the amount of lung fluid.

Exemplary additional features include one or more of:
Estimating a level of fluid within the digestive system based on an analysis of the applied alternating current and measured voltage drop. The enteral feeding rate may be automatically adjusted according to the estimated fluid level, for example, to prevent reflux. Additional details of exemplary systems and/or methods for estimating fluid levels based on impedance measurements computed based on electrode(s) located on a tube positioned within the esophagus may be found with reference to International Patent Application No. IL2015/051156, by the same inventors of the present application.
Monitoring a position of the tube within the digestive system based on an analysis of the applied alternating current and measured voltage drop. For example, to detect when the tube moves out of the correct position. Additional details of exemplary systems and/or methods for monitoring the position of a tube based on impedance measurements computed based on electrode(s) located on a tube positioned within the esophagus may be found with reference to U.S. Pat. No. 9,713,579, by the same inventors of the present application.
Detecting a gastric reflux event based on an analysis of the applied alternating current and measured voltage drop. For example, to stop enteral feeding. Optionally, when a gastric reflux event is detected, the estimation of lung fluid may be stopped and/or adjusted to account for the gastric reflux event, for example, by subtracting the computed impedance value (denoting total impedance due to lung fluid and reflux) from the estimated impedance value due to the presence of fluid in the esophagus due to the reflux. When no gastric reflux event is detected, the measured impedance may be assumed to be an indication of lung fluid without interference effects due to the presence of fluid within the esophagus (i.e., the reflux). Additional details of exemplary systems and/or methods for detecting reflux event based on impedance measurements computed based on electrode(s) located on a tube positioned within the esophagus may be found with reference to International Patent Application No. IL2017/050634, by the same inventors of the present application.

Estimate functionality of lung(s) according to a correlation between impedance values and lung function, and/or a correlation between lung fluid and lung function. As lung fluid increases, the functionality of the lungs decreases. Functionality of the lungs may be for example, in terms of oxygen and carbon dioxide exchange, and/or air volume capacity of the lungs. Oxygen and carbon dioxide exchange is decreased due to the amount of tissue available to perform the exchange, since fluid filled tissue (i.e., pulmonary edema) cannot perform such exchange. Alternatively or additionally, the lung may be compressed from external fluid (e.g. pulmonary effusion) which reduces the volume of air capacity of the lung, reducing lung efficiency. The estimate of lung fluid (e.g., amount of fluid, change relative to a baseline) may be correlated to lung function, for example, according to a graph and/or function, which may be empirically measured and/or computed based on mathematical models. The estimated lung function may be computed as a change relative an initial baseline (e.g., 100%). For example, a certain increase in lung fluid may correspond to a 10% decrease in lung function. In another example, a 15% decrease in impedance may correspond to a 5% decrease in lung function.

At 118, acts 106-117 are iterated over time as part of the process of monitoring the patient for accumulation of clinically significant amount of lung fluid. Each iteration generates a current (i.e., real-time) impedance value and/or impedance score indicative of the current amount of lung fluid. The impedance values and/or scores may be plotted as points on the graph. The trend line may be dynamically computed according to the most recent points on the graph, for example, according to a sliding window. The GUI may be dynamically updated as new points are plotted and/or as the trend line and/or extension of the trend line are dynamically updated based on the sliding window.

The monitoring may continue for example, as long as the tube is in use for other purposes, for example, for enteral feeding of the patient and/or for draining excess fluid from the stomach of the patient. For example, monitoring for accumulation of lung fluid of an intubated patient being enterally fed by an enteral feeding over a period of 72 hours.

Figure 11:
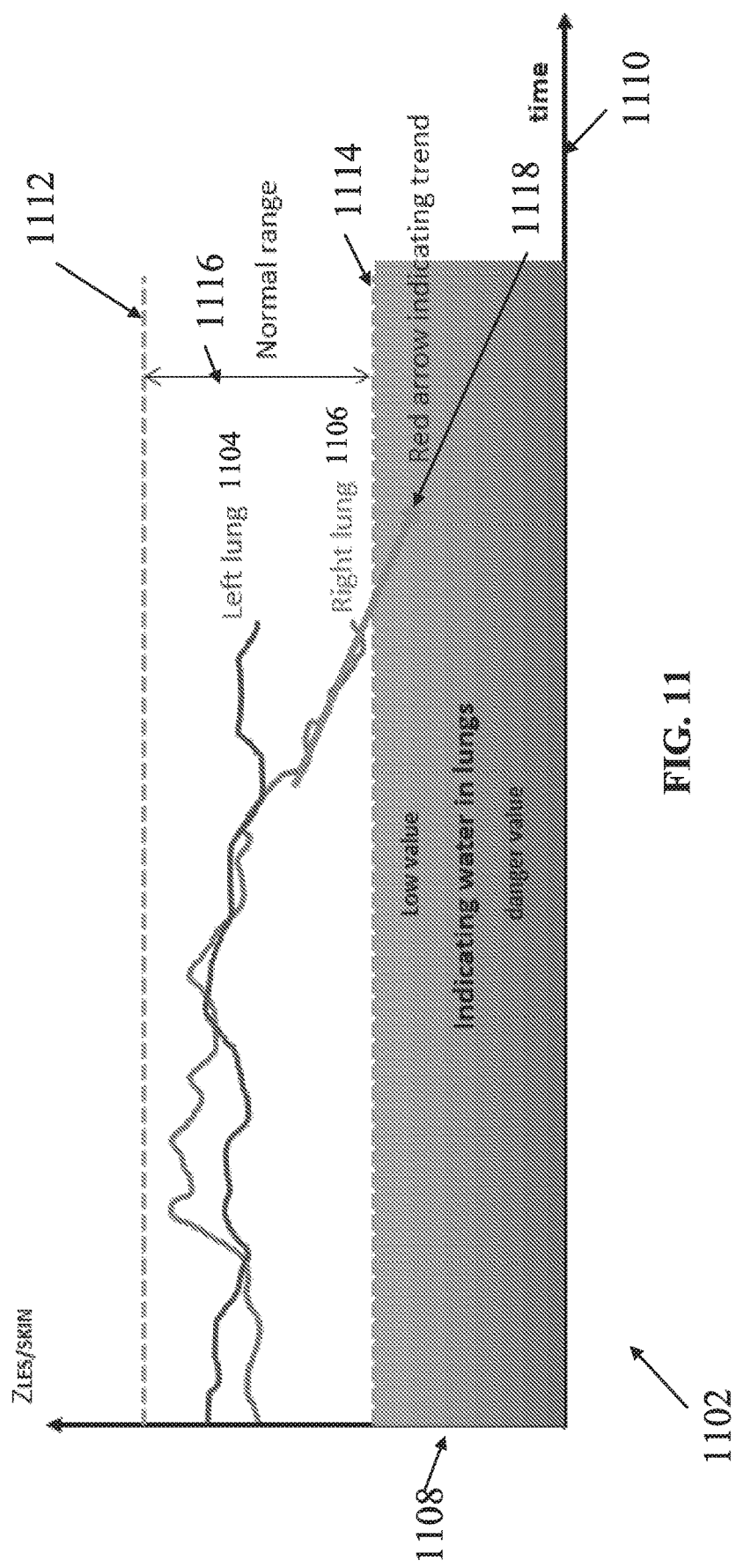
FIG. 11 is a schematic of an exemplary graph presented on a display indicative of the sensed lung fluid, in accordance with some embodiments of the present invention.

Reference is now made to FIG. 11, which is a schematic of an exemplary graph 1102 presented on a display indicative of the sensed lung fluid, in accordance with some embodiments of the present invention. Graph 1102 presents a curve indicative of the sensed fluid for a left lung 1104 and a right lung 1106. Curves 1104 1106 are plotted along an impedance score axis 1108 (along the y-axis) as a function of time 1110 (along the x-axis). Curves 1104 and 1106 are dynamically updated in real time, as new impedance values are computed.

The impedance score is computed based on the complex impedance value. The impedance score may be computed, for example, as the vector length of a vector representation of the complex impedance value, the value of the real component of the complex impedance value, and/or the value of the imaginary component of the complex impedance value. The impedance score may be computed as an aggregation of multiple sub-impedance scores each computed for an impedance value measured at a certain AC frequency. Alternatively or additionally, the impedance score may be computed as an aggregation of multiple sub-impedance scores each computed for a distinct pair of electrodes, when the feeding tube includes multiple intra-body electrodes and/or when multiple extracorporeal electrodes are positioned on the skin of the patient.

Graph 1102 includes a normal threshold 1112 denoting a lung without fluid, and/or with a normal amount of fluid, and/or with a clinically insignificant amount of fluid, and include a clinically significant amount of lung fluid threshold 1114 denoting a lung with a clinically significant amount of fluid. A region 1116 between thresholds 1112 and 1114 denotes a lung that is at impending risk of accumulating a clinically significant amount of fluid, but is currently determined as being normal or having a clinically insignificant amount of fluid. Thresholds 1112 and 1114 correspond to thresholds 1010 and 1012 described with reference to FIG. 10, which are adjusted according to the method used to convert the impedance value to an impedance score.

A trend indication 1118 is computed and plotted on graph 1102, for example, as a trend line. The trend line 1118 may be dynamically computed and adjusted, for example, based on a sliding window on a recent time interval. Trend line 1118 may be computed as a line that is best fitted to the plotted impedance scores according to a least square fit.

Optionally, trend line 1118 is extrapolated to predict a risk of impending accumulation of clinically significant amount of lung fluid. Trend line 1118 may be extended past the last plotted point according to the most recent impedance measurement. The extension may be for a predefined time interval, for example, the next 30 minutes, 60 minutes, 120 minutes, 6 hours, 12 hours, or 24 hours, or other values. An extension that falls below threshold 1114 is indicative that the patient is trending towards accumulating a clinically significant amount of fluid in the lung(s).

Various embodiments and aspects of the systems, methods, apparatus, and/or code instructions delineated hereinabove and as claimed in the claims section below find experimental support in the following example.

EXAMPLE

Reference is now made to the following example, which together with the above descriptions illustrates some implementations of the systems, methods, apparatus, and/or code instructions described herein, in a non limiting fashion.

An experimental set-up for sensing lung fluid based on at least one intra-body sensor positioned in proximity and/or in contract with the LES is now described.

An intra-body sensor is positioned in proximity to and/or in contact with the LES within the esophagus of organs extracted from an animal. Three clips representing extracorporeal electrode(s) were attached to a lower lobe of a left lung at locations denoted as LL1 (within the upper portion of the lung), LL2 (within the middle portion of the lung), and LL3 (within the lower portion of the lung).

A first set of baseline impedance measurements were obtained by applying one or more alternating currents and measuring the voltage between each electrode at locations LL1-LL3 and the intra-body electrode. The baseline impedance values were converted to an impedance score, representing a relative initial real number. The baseline impedance score of the highest impedances at LL2 and LL3 was set to 1000. The baseline impedance score of LL1 was set relative to the baseline scores of LL2 and LL3 as 850.

Fluid was administered into the lung three times:
  40 cc (cubic centimeters) were injected close to the electrode at location LL2.

40 cc (cubic centimeters) were injected close to the electrode location LL3.

10 cc of fluid was poured into the lung.

Impedance values were computed after each administration of fluid, with respect to each electrode, and converted to impedance scores representing a value relative to the baseline of 1000.

After a time interval of 2-3 minutes, impedance values were computed with respect to each electrode, and converted to impedance scores representing a value relative to the baseline of 1000.

The results are presented in the table below:

|  | Baseline | 40 cc close to LL2 | 40 cc close to LL3 | Poured 10 cc into lung | Waited 2-3 minutes |
| --- | --- | --- | --- | --- | --- |
| LL1 (upper) | 850 | 700-750 | 650-700 | 600 | 400 |
| LL2 (middle) | 1000 | 750 | 700-760 | 800 | 400 |
| LL3 (lower) | 1000 | 1000 | 590-610 | 410 | 380-350 |

The experimental results illustrate that impedance values measured by intra-corporeal electrode(s) positioned within the esophagus and/or stomach in proximity to and/or in contact with the LES and by one or more extracorporeal electrode(s) optionally positioned in proximity to the lung(s) provide an indication of lung fluid, optionally an indication of clinically significant amount of lung fluid.

Alternatively or additionally, the above values may be indicative of lung function, where 1000 denotes a baseline, and values below 1000 indicate a corresponding decrease in lung function.

Figure 12:
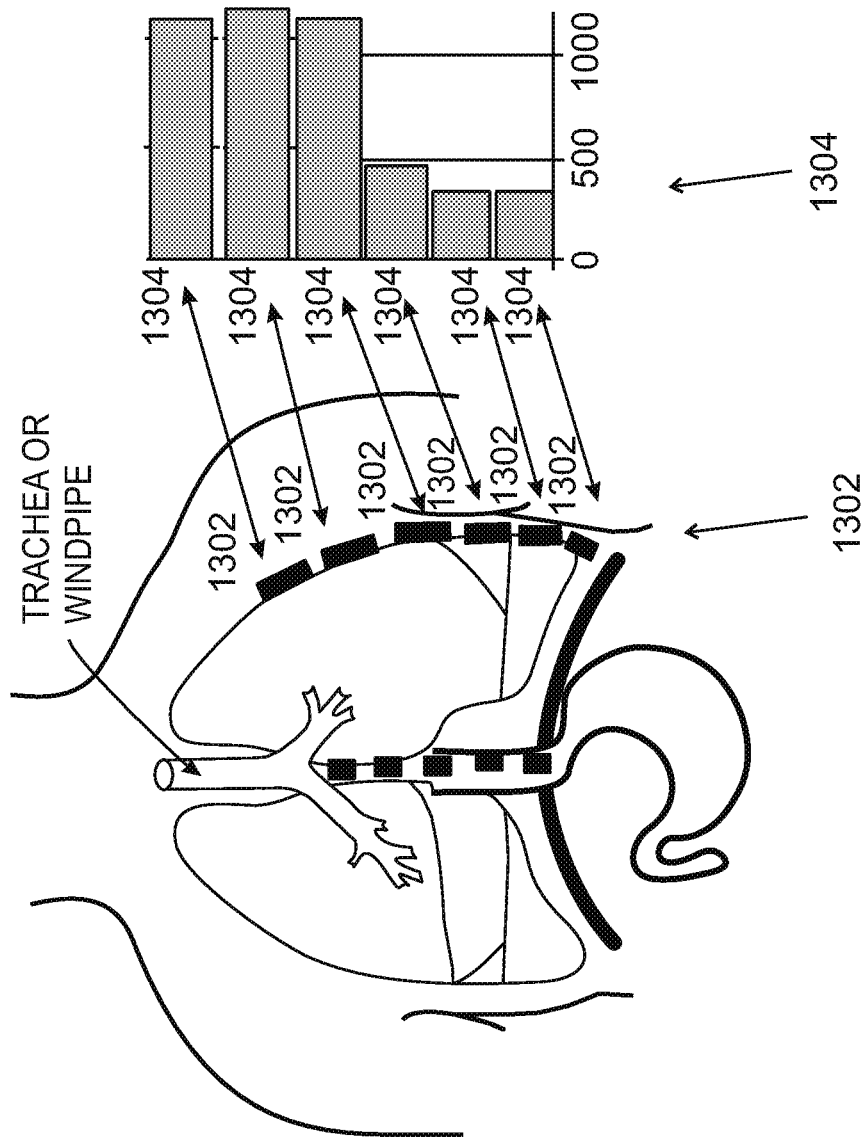
FIG. 12 is a schematic depicting an exemplary computed lung function and/or lung fluid map for presentation on a display of a client terminal (e.g., within a GUI), in accordance with some embodiments of the present invention.

Reference is now made to FIG. 12, which is a schematic depicting an exemplary computed lung function and/or lung fluid map for presentation on a display of a client terminal (e.g., within a GUI), in accordance with some embodiments of the present invention. The map includes, for one or more anatomical locations 1302 (e.g., lung lobes) indications 1304 of corresponding impedance scores relative to a baseline, where the baseline is indicative of normal or an initial state of the patient being monitored. Value below the baseline are indicative of a decrease in lung function and/or an increase in lung fluid, according to the selected mapping between impedance values and lung function and/or impedance values and lung fluid.

The map may include numerical values of the relative impedance scores and/or functional values and/or change in lung fluid corresponding to anatomical locations, and/or color coding of the anatomical locations according to the scores and/or values and/or change in lung fluid and/or a graph indicative the values. The map visually identifies which areas of the lung are experiencing a relative decrease in function and/or an increase in lung fluid.

For example, as shown in FIG. 12, indications 1304 include a color coded bar graph, where each bar corresponds to a different anatomical location of the lung(s), and colors are indicative of severity, for example, green is indicative of normal and/or no significant change from baseline, orange is indicative of mild severity and/or not very significant change from baseline, and red is indicative of high severity and/or significant change from baseline.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant sensors and electrodes will be developed and the scope of the terms sensor and electrode is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An apparatus for protecting a heart of a target patient from current during current based lungs monitoring of the target patient for accumulation of lung fluid at a base of at least one lung, the apparatus comprising:
    a feeding tube for insertion into a distal end of an esophagus of the target patient;
    at least one first electrode disposed on a distal end of the feeding tube at a location such that the at least one first electrode is located at the distal end of the esophagus of the target patient when the feeding tube is located within the esophagus and in use and, wherein the at least one first electrode is positioned for electrical contact with a tissue of the esophagus below a level of the heart including a lower esophageal sphincter (LES) and tissue in proximity to the LES while the feeding tube is in use for enteral feeding via a stomach and/or a digestive system of the patient;
    at least one second electrode sized and shaped for contacting a surface of a skin of the target patient below the level of the heart, wherein a straight line connecting at least one pair of the at least one first electrode located at the distal end of the esophagus of the target patient below the level of the heart, and the at least one second electrode, located on the surface of the skin of the target patient below the level of the heart passes through the base of the lung while excluding the heart of the patient, the straight line representing flow of a non-cardiac current channel between the at least one pair of the at least one first electrode and the at least one second electrode that avoids or reduces the current through the heart; and
    a non-transitory memory having stored thereon a code for execution by at least one hardware processor of a computing device, the code including instruction for establishing the non-cardiac current channel that avoids or reduces current through the heart between the at least one pair of the at least one first electrode, located at the distal end of the esophagus of the target patient below the level of the heart, and the at least one second electrode, located on the surface of the skin of the target patient below the level of the heart, by
    (1) applying at least one alternating current of the non-cardiac current channel to the at least one pair of the at least one first electrode and the at least one second electrode,
    (2) measuring a voltage over the at least one pair of the at least one first electrode and the at least one second electrode, and
    (3) computing an estimate of a change of the lung fluid at the base of the at least one lung relative to a baseline in the at least one lung of the target patient according to the applied at least one alternating current of the non-cardiac current channel and the measured voltage;
    wherein the applying the at least one alternating current of the non-cardiac current channel, the measuring the voltage drop, and the computing the estimate of the change in the lung fluid are iteratively executed for monitoring the target patient for the accumulation of the lung fluid at the base of the at least one lung while the feeding tube is in use,
    wherein the lung fluid is of non-gastric origin.

2. The apparatus according to claim 1, wherein the applying, the measuring, and the computing are continuously executed for continuous monitoring of the target patient for the accumulation of the lung fluid.

3. The apparatus according to claim 1, wherein the at least one first electrode is disposed on the distal end of the feeding tube at a location such that the at least one electrode is located at least one of: in proximity to the LES and in contact with the LES of the target patient.

4. The apparatus according to claim 1, wherein the feeding tube includes at least one of:
    an enteral feeding tube having a distal end designed for positioning within at least one of the stomach and intestines when in use for enteral feeding;
    a nasogastric tube having a distal end designed for positioning within at least one of the stomach and intestines when in use.

5. The apparatus according to claim 1, wherein the at least one first electrode is associated with a clip-on attachment mechanism that attaches to an off-the-shelf feeding tube.

6. The apparatus according to claim 1, wherein the feeding tube includes a catheter having at least one lumen that includes wires for transmission of signals between the at least one first electrode and an externally located the at least one hardware processor.

7. The apparatus according to claim 1, wherein the at least one first electrode is mounted on an inflatable balloon located at the distal end of the feeding tube, wherein when the inflatable balloon is inflated the at least one first electrode contacts an inner wall of the esophagus.

8. The apparatus according to claim 1, wherein the at least one first electrode and the at least one second electrode include electrodes for generating the at least one alternating current of the non-cardiac current channel and for sensing the generated at least one alternating current.

9. The apparatus according to claim 1, wherein the at least one second electrode includes at least one pad electrode designed for contacting the skin of the target patient.

10. The apparatus according to claim 1, wherein the computing the estimate of the change of the lung fluid of the target patient according to the applied at least one alternating current of the non-cardiac current channel is indicative of pulmonary edema at a certain lung lobe when the at least one second electrode is positioned on the skin of the target patient corresponding to the certain lung lobe.

11. The apparatus according to claim 1, wherein the computing the estimate, based on initial base measurement of the change in the lung fluid in the at least one lung of the target patient according to the applied at least one alternating current of the non-cardiac current channel is indicative of pulmonary effusion of a certain lung when the at least one second electrode is positioned on the skin of the target patient corresponding to the base of the certain lung.

12. The apparatus according to claim 1, further comprising code for differentiating between pulmonary edema and pleural effusion according to an analysis of impedance values measured by the at least one second electrode located on the skin of the target individual corresponding to the base of the at least one lung and impedance values measured by another at least one second electrode located on the skin of the target individual corresponding to one or more lobes of the at least one lung.

13. The apparatus according to claim 1, further comprising code instructions for estimating changes in level of fluid within the digestive system based on an analysis of the applied alternating current and measured voltage drop.

14. The apparatus according to claim 1, further comprising code instructions for monitoring a position of the feeding tube within the digestive system based on an analysis of the applied at least one alternating current of the non-cardiac current channel and measured voltage drop.

15. The apparatus according to claim 1, further comprising code instructions for detecting a gastric reflux event based on an analysis of the applied the applied at least one alternating current of the non-cardiac current channel and measured voltage drop and distinguishing the reflux event from lung fluid changes.

16. The apparatus according to claim 1, further comprising code instructions for at least one of:
estimating a change in lung function relative to a lung function baseline according to a correlation between the change in the lung fluid and lung function; and
comparing lung fluid changes between the left and right lung for differentiation between lung fluid processes that affect both lungs from lung fluid processes that affect one lung more than the other.

17. The apparatus according to claim 1, wherein the amount of lung fluid is estimated for the left lung and right lung of the target patient according to measurements performed by a same set of common at least one first electrode, and a left set of the at least one second electrode positioned on the left side of the target patient in proximity to the left lung and a right set of the at least one second electrode positioned on the right side of the target patient in proximity to the right lung and the same set of common at least one first electrodes.

18. The apparatus according to claim 1, wherein an estimated amount of lung fluid in the at least one lung of the target patient is computed based on impedance values computed according to the applied at least one alternating current of the non-cardiac current channel and the measured voltage.

19. The apparatus according to claim 18, further comprising code for mapping the impedance values to an indication of clinically significant amount of lung fluid.

20. The apparatus according to claim 1, wherein an amount of the lung fluid is estimated according to a reference set of base values measured from a plurality of sampled individuals that map between measured impedance values and amounts of lung fluids.

21. The apparatus according to claim 1, wherein an amount of the lung fluid is estimated by code for:
computing at least one impedance value corresponding to the at least one frequency of the applied at least one alternating current of the non-cardiac current channel;
converting the computed at least one impedance value to an impedance score associated with a time stamp indicative of the time of application of the at least one applied alternating current of the non-cardiac current channel; and
presenting the impedance score as a value on a graph within a graphical user interface (GUI) displayed on a display of a client terminal, wherein an x-axis of the graph denotes the time of application of the at least one applied current and a y-axis of the graph denotes the impedance score.

22. The apparatus according to claim 1, further comprising code for computing a baseline impedance value indicative of a first amount of fluid in the at least one lung denoted as clinically insignificant, and monitoring measured impedance values to detect a drop in the impedance value below a threshold indicative of a second amount of fluid in the at least one lung denoted as clinically significant.

23. The apparatus according to claim 1, further comprising code for generating an alert when a set of rules is met indicative of an impending accumulation of clinically significant amount of lung fluid according to a defined risk threshold, and transmitting the alert for presentation on at least one of: a client terminal, a mobile device, and a server; wherein a probability of the impending accumulation of clinically significant amount of lung fluid is computed according to a direction of a trend line towards a threshold denoting the accumulation of clinically significant amount of lung fluid, the trend line computed based on a plurality of impedance values measured over a recent time interval.

24. The apparatus of claim 1, wherein the lung fluid of non-gastric origin consists of pleural effusion.

25. The apparatus of claim 1, wherein the non-gastric origin is selected from a group consisting of: cardiac failure, liver failure, renal failure, sudden severe episode of upper airway obstruction, and post surgical relief of chronic upper airway obstruction.

26. A method for protecting a heart of a target patient from current during sensing lung fluid for the target patient at a base of the lungs, the method comprising:
applying at least one alternating current below a level of the heart to at least one first electrode,
wherein the at least one first electrode is disposed on a distal end of a feeding tube sized and shaped for insertion into a distal end of an esophagus of the target patient, at a location such that the at least one first electrode is located at the distal end of the esophagus of the target patient when the feeding tube is located within the esophagus and in use, wherein the at least one first electrode is positioned for electrical contact with tissue of the esophagus including a lower esophageal sphincter (LES) and tissue in proximity to the LES while the feeding tube is in use for enteral feeding via a stomach and/or a digestive system of the patient;
establishing a non-cardiac current channel that avoids or reduces current through the heart between at least one pair of the at least one first electrode, located at the distal end of the esophagus of the target patient below the level of the heart, and the at least one second electrode, located on a surface of skin of the target patient below the level of the heart,
measuring a voltage drop between the at least one pair of the at least one first electrode and the at least one second electrode, wherein the at least one second electrode is sized and shaped for contacting the surface of the skin of the target patient below the level of the heart, wherein a straight line connecting the at least one pair of the at least one first electrode, located at the distal end of the esophagus of the target patient below the level of the heart, and the at least one second electrode, located on the surface of the skin of the target patient below the level of the heart, passes through the base of the lung while excluding the heart of the patient, the straight line representing flow of the non-cardiac current channel between the at least one pair of the at least one first electrode and the at least one second electrode that avoids or reduces the current through the heart; and computing an estimate of a change of lung fluid at the base of at least one lung relative to a baseline in the at least one lung of the target patient according to the applied at least one alternating current of the non-cardiac current channel and the measured voltage drop, wherein the applying the at least one alternating current of the non-cardiac current channel, measuring the voltage drop, and the computing the estimate of the change of lung fluid are iteratively executed for monitoring the target patient while the feeding tube is in use, wherein the lung fluid is of non-gastric origin.

* * * * *